United States Patent
Hatakeyama et al.

(10) Patent No.: US 11,802,258 B2
(45) Date of Patent: Oct. 31, 2023

(54) PERFUME PRECURSOR

(71) Applicant: TAKASAGO INTERNATIONAL CORPORATION, Tokyo (JP)

(72) Inventors: Tadahide Hatakeyama, Kanagawa (JP); Shinya Yamada, Kanagawa (JP); Masato Murai, Kanagawa (JP); Takahiro Ishikawa, Kanagawa (JP)

(73) Assignee: TAKASAGO INTERNATIONAL CORPORATION, Tokyo (JP)

(*) Notice: Subject to any disclaimer, the term of this patent is extended or adjusted under 35 U.S.C. 154(b) by 0 days.

(21) Appl. No.: 16/650,297

(22) PCT Filed: Sep. 21, 2018

(86) PCT No.: PCT/JP2018/035183
§ 371 (c)(1),
(2) Date: Mar. 24, 2020

(87) PCT Pub. No.: WO2019/059375
PCT Pub. Date: Mar. 28, 2019

(65) Prior Publication Data
US 2021/0214644 A1    Jul. 15, 2021

(30) Foreign Application Priority Data
Sep. 25, 2017 (JP) .................................. 2017-184026

(51) Int. Cl.
| C11B 9/00 | (2006.01) |
| A61K 8/34 | (2006.01) |
| A61K 8/37 | (2006.01) |
| A61Q 15/00 | (2006.01) |
| C11D 3/00 | (2006.01) |
| C11D 3/50 | (2006.01) |

(52) U.S. Cl.
CPC ............ *C11B 9/0061* (2013.01); *A61K 8/347* (2013.01); *A61K 8/37* (2013.01); *A61Q 15/00* (2013.01); *C11D 3/0015* (2013.01); *C11D 3/50* (2013.01); *A61K 2800/77* (2013.01)

(58) Field of Classification Search
CPC .................................................... C11B 9/0061
See application file for complete search history.

(56) References Cited

U.S. PATENT DOCUMENTS

| 4,168,248 A | 9/1979 | Kulka |
| 5,172,704 A | 12/1992 | Chan et al. |
| 5,228,461 A | 7/1993 | Chan et al. |
| 6,207,857 B1 | 3/2001 | Anderson et al. |
| 6,232,487 B1 | 5/2001 | Anderson et al. |
| 6,576,247 B1 | 6/2003 | Ikemoto et al. |
| 6,787,674 B1* | 9/2004 | Taneja .................. C11B 9/0034 554/8 |
| 2002/0032132 A1 | 3/2002 | Frerot et al. |
| 2002/0054893 A1 | 5/2002 | Ishida et al. |
| 2002/0169087 A1 | 11/2002 | Herrmann et al. |
| 2003/0083376 A1 | 5/2003 | Eh et al. |
| 2003/0148901 A1 | 8/2003 | Frerot et al. |
| 2004/0102357 A1 | 5/2004 | Smith et al. |
| 2004/0248762 A1 | 12/2004 | McGee et al. |
| 2006/0159639 A1 | 7/2006 | Ogura et al. |
| 2006/0210503 A1 | 9/2006 | Turin |
| 2009/0202464 A1 | 8/2009 | Flachsmann |
| 2011/0015421 A1 | 1/2011 | Abe et al. |
| 2012/0195844 A1 | 8/2012 | Fankhauser et al. |
| 2013/0280185 A1* | 10/2013 | Subramanyam ........ A61P 17/10 424/52 |
| 2014/0023598 A1 | 1/2014 | Smith et al. |
| 2014/0031270 A1 | 1/2014 | Flachsmann |
| 2014/0056825 A1 | 2/2014 | Smith et al. |
| 2014/0056826 A1 | 2/2014 | Smith et al. |

(Continued)

FOREIGN PATENT DOCUMENTS

| CN | 1200028 A | 11/1998 |
| CN | 1741784 A | 3/2006 |

(Continued)

OTHER PUBLICATIONS

Extended European Search Report dated May 12, 2021, issued by the European Patent Office in counterpart European patent Application No. 18858666.3.

Muniz, Kiilian et al., "Diamination of Olefins: Synthesis, Structures and Reactivity of Osmaimidazolidines", Chemistry—A European Journal, 2003, vol. 9, No. 22, pp. 5581-5596. (16 pages total).

Cutler, S.J. et al., "The Synthesis and Biological Evaluation of Eugenol Derivatives as Potential Herbicidal Agents", Proceedings—Plant Growth Regulation Society of America, 2002, 29th, pp. 93-98. (6 pages total).

Foote, P. A., "Derivatives of Para-Methoxycinnamic Acid", Journal of the American Pharmaceutical Association, 1928, vol. 17, pp. 958-962. (5 pages total).

(Continued)

*Primary Examiner* — Arrie L Reuther
(74) *Attorney, Agent, or Firm* — Sughrue Mion, PLLC

(57) ABSTRACT

A fragrance precursor represented by formula (1):

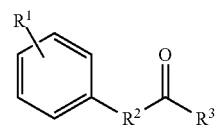

wherein $R^1$ represents a hydrogen atom, an alkyl group having a carbon number of 1 to 12, a hydroxy group, a methoxy group or an ethoxy group $R^2$ represents a single bond, an alkylene group having a carbon number of 1 to 2, which may have a substituent, or a vinylene group which may have a substituent; and $R^3$ represents a residue resulting from removal of one hydrogen atom of a hydroxy group from a fragrance alcohol having a carbon number of 5 to 20 or a phenol which may have a substituent.

1 Claim, No Drawings

(56) References Cited

U.S. PATENT DOCUMENTS

| | | | |
|---|---|---|---|
| 2014/0065081 A1 | 3/2014 | Smith et al. | |
| 2015/0247109 A1 | 9/2015 | Flachsmann | |
| 2016/0089462 A1* | 3/2016 | Frankenbach | G16C 20/40 |
| | | | 424/76.8 |
| 2016/0286753 A1 | 10/2016 | Flachsmann | |

FOREIGN PATENT DOCUMENTS

| | | |
|---|---|---|
| CN | 101472874 A | 7/2009 |
| CN | 101970594 A | 2/2011 |
| CN | 103261138 A | 8/2013 |
| CN | 106866419 A | 6/2017 |
| EP | 0 760 243 A1 | 3/1997 |
| EP | 0 887 335 A1 | 12/1998 |
| EP | 0955035 A1 | 11/1999 |
| EP | 1 169 292 B1 | 11/2004 |
| JP | 3-297685 A | 12/1991 |
| JP | 4-337395 A | 11/1992 |
| JP | 5-148190 A | 6/1993 |
| JP | 9-132527 A | 5/1997 |
| JP | 9-241116 A | 9/1997 |
| JP | 11-147852 A | 6/1999 |
| JP | 11-286428 A | 10/1999 |
| JP | 11-512132 A | 10/1999 |
| JP | 2000-512663 A | 9/2000 |
| JP | 2002-88391 A | 3/2002 |
| JP | 2002-540184 A | 11/2002 |
| JP | 2003-55314 A | 2/2003 |
| JP | 2003-160792 A | 6/2003 |
| JP | 2004-107207 A | 4/2004 |
| JP | 2004-262900 A | 9/2004 |
| JP | 2004-315502 A | 11/2004 |
| JP | 2007-290983 A | 11/2007 |
| JP | 2008-530196 A | 8/2008 |
| JP | 2008-280318 A | 11/2008 |
| JP | 2009-46442 A | 3/2009 |
| JP | 2012-97367 A | 5/2012 |
| JP | 2017-179670 A | 10/2017 |
| WO | 96/14827 A1 | 5/1996 |
| WO | 97/07778 A1 | 3/1997 |
| WO | 97/30687 A2 | 8/1997 |
| WO | 2008/032847 A1 | 3/2008 |
| WO | 2011/055251 A1 | 5/2011 |
| WO | 2016/113151 A1 | 7/2016 |
| WO | 2018/135647 A1 | 7/2018 |

OTHER PUBLICATIONS

Carestia, Anthony M. et al, "Reagent-dictated site selectivity in intermolecular aliphatic C—H functionalizations using nitrogen-centered radicals", Chemical Science, May 14, 2018, Vo. 9, No. 24, pp. 5360-5365. (6 pages total).

International Search Report (PCT/ISA/210) dated Dec. 18, 2018 by the International Searching Authority in counterpart International Patent Application No. PCT/JP2018/035183.

Written Opinion (PCT/ISA/237) dated Dec. 18, 2018 by the International Searching Authority in counterpart International Patent Application No. PCT/JP2018/035183.

Communication dated Jul. 21, 2022 issued by China National Intellectual Property Administration in corresponding Chinese application No. 201880061087.X.

Communication issued by the European Patent Office dated May 4, 2023 in European Patent Application No. 18858666.3.

\* cited by examiner

PERFUME PRECURSOR

TECHNICAL FIELD

The present invention relates to a fragrance precursor, a method for releasing a fragrance alcohol, a phenol or a phenol derivative by the action of a hydrolase or microorganism, a novel compound, a fragrance composition containing the novel compound, and an aroma product, laundry care product, hair care product, cosmetic, cleaner or deodorant containing the fragrance composition.

BACKGROUND ART

In recent years, with an increased consumer's interest in scents, a wide range of demands are placed on the scent at the time of using a product. In regard to the needs for improvement of the scent longevity, compounded fragrances or fragrance capsules, in which a lot of a last note component with low volatility is blended, are used in general.

As a scent longevity-enhancing agent, for example, a fixative such as p-menthane-3,8-diol (Patent Literature 1) and 3-(menthoxy)-1,2-propanediol (Patent Literature 2) has been proposed.

In addition, due to an increased interest in hygiene, many people have become sensitized to "a smell in living space" and consequently, even a smell that they have been heretofore not aware of in life often assumes a target malodor. Among these, malodors associated with human body or laundry are known to be mainly caused by a microorganism. As the method for deodorizing these malodors, there have been proposed, for example, a method of suppressing proliferation of a microorganism by using an antimicrobial (Patent Literature 3), and a method of sensuously alleviating unpleasant sensation by using a fragrance (Patent Literatures 4 and 5).

CITATION LIST

Patent Literature

Patent Literature 1: JP-A-4-337395
Patent Literature 2: JP-A-2002-88391
Patent Literature 3: JP-A-2009-46442
Patent Literature 4: JP-A-2004-315502
Patent Literature 5: JP-A-11-286428

SUMMARY OF INVENTION

Technical Problem

However, with respect to the improvement of the scent longevity, when a compounded fragrance is used in a product, for example, after clothing or hair is cleaned with a cleaner, most of fragrance components are washed away into water together with cleaning components such as surfactant and therefore, only a very small amount of fragrance components remain in clothing or hair.

In addition, many fragrance components are volatilized in drying step after the cleaning, as a result, the lingering scent intensity is reduced. Furthermore, since the lingering scent component is biased toward a fragrance component having an extremely low volatility, the palatability is likely to deteriorate, and an unpleasant sensation is sometimes caused.

When a fragrance capsule is used, the lingering scent may be enhanced, but stabilization in a product is difficult, and the application field is limited. In addition, in the case of the fragrance capsule, a scent is not released unless the capsule is physically broken and therefore, scent emission may occur when a lingering scent is not needed, or a scent is not emitted when a lingering scent is needed. Accordingly, there is a problem of mismatch between the need for a scent and the timing of emitting a scent from the capsule.

In addition, when a fixative is used as a scent longevity-enhancing agent together with a compounded fragrance, the scent lingering property may be somewhat enhanced, but a fully satisfactory lingering scent longevity has not been obtained.

Furthermore, since the lingering scent component is still biased toward a low-volatile component even when a fixative is used, use of a fixative does not lead to an improvement of the smell quality of the lingering scent, and a lingering scent retaining technique for allowing an aroma with fresher feeling to last is demanded.

As to the method for deodorizing a malodor caused by a microorganism, when an antimicrobial is used in a personal care product such as deodorant agent, not only bacteria causing a malodor but also skin-resident bacteria useful for skin are killed at the same time, and the skin flora balance may be lost. The skin-resident bacteria also fulfill the role of keeping the pH weakly acidic and preventing skin infections and in view of maintaining the health of the skin, frequent use of an antimicrobial is not necessarily favorable.

In addition, after washing clothing or hair with a cleaner containing an antimicrobial, most of the antimicrobial components are washed away into water together with cleaning components such as surfactant and therefore, only a very small amount of antimicrobial components remain in clothing or hair. In order to kill the malodor-causing bacteria to such an extent that an unpleasant odor is not sensed, a large amount of antimicrobial or an antimicrobial having a high bactericidal effect needs to be used, and this may raise the concern of adverse effect on human body or environment and at the same time, be associated with a rise in the cost.

Furthermore, in the case of using a fragrance as a sensory deodorant, this is effective in the short term, but since the scent intensity weakens due to volatilization of a fragrance component with time, the deodorizing effect does not last.

Moreover, as for the malodor caused by a microorganism, the odor intensity and unpleasant sensation are strengthened along with the progress of proliferation of a microorganism, and it is likely that when the consumer truly needs the deodorizing effect, a sufficient deodorizing effect is not obtained due to a weak lingering scent intensity of the fragrance. The scent lingering property may be increased with the purpose of enhancing the continuity of deodorizing effect, but since the fragrance composition is biased toward a fragrance component having an extremely low volatility, the palatability is likely to deteriorate, and an unpleasant sensation is sometimes caused.

It may also be conceived to use a fragrance having a high scent intensity or extremely raise the perfuming amount, but, for example, at the start of use of a deodorant product, during use of a body cleaner, or during drying of clothing, the fragrance smells too strong, and the user may feel sick.

Accordingly, for the malodor caused by a microorganism, a deodorization technique for enabling a deodorizing effect to be exerted at the same timing as a time at which a microorganism sufficiently proliferates and generates a malodor is demanded.

The present invention has been made in consideration of these conventional circumstances, and the problem to be solved is to provide a fragrance precursor capable of continuously supplying an aroma with fresh feeling even after cleaning the clothing or hair by use of a cleaner or after passing a drying step following the cleaning.

In addition, the problem to be solved by the present invention is to provide a technique for enabling scent emission or deodorization to be achieved at the same timing as a time at which a microorganism sufficiently proliferates and generates a malodor.

Solution to Problem

As a result of intensive studies to solve the problems above, the present inventors have found that a compound having a specific structure releases a fragrance alcohol, a phenol or a phenol derivative by the action of a hydrolase or microorganism and thereby, realizes an increase in the lingering scent longevity with fresh feeling and alleviation of an odor caused by a microorganism. The present invention has been accomplished based on this finding.

More specifically, the present invention relates to the following [1] to [8].

[1] A fragrance precursor represented by the following formula (1).

[Chem. 1]

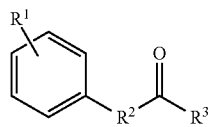

(1)

(In the formula (1), $R^1$ represents a hydrogen atom, an alkyl group having a carbon number of 1 to 12, a hydroxy group, a methoxy group or an ethoxy group, $R^2$ represents a single bond, an alkylene group having a carbon number of 1 to 2 which may have a substituent, or a vinylene group which may have a substituent, and $R^3$ represents a residue resulting from removal of one hydrogen atom of a hydroxy group from a fragrance alcohol having a carbon number of 5 to 20 or a phenol which may have a substituent.)

[2] A method for releasing a fragrance alcohol, a phenol or a phenol derivative, including a step of reacting the fragrance precursor according to [1] with a hydrolase.

[3] The method for releasing a fragrance alcohol, a phenol or a phenol derivative according to [2], in which the hydrolase is a lipase.

[4] A method for releasing a fragrance alcohol, a phenol or a phenol derivative, including a step of reacting the fragrance precursor according to [1] with a microorganism.

[5] The method for releasing a fragrance alcohol, a phenol or a phenol derivative according to [4], in which the microorganism is at least one species selected from the group consisting of *Staphylococcus aureus*, *Staphylococcus epidermidis*, *Corynebacterium xerosis*, *Pseudomonas aeruginosa*, *Bacillus subtilis*, *Moraxella osloensis*, *Propionibacterium acnes*, and *Malassezia furfur*.

[6] At least one compound selected from the group consisting of the later-described compounds 001 to 118.

[7] A fragrance composition containing the compound according to [6].

[8] An aroma product, laundry care product, hair care product, cosmetic, cleaner or deodorant containing the compound according to [6] or the fragrance composition according to [7].

Advantageous Effects of Invention

According to the present invention, a fragrance precursor capable of continuously supplying an aroma with fresh feeling even after cleaning the clothing or hair by use of a cleaner or after passing a drying step following the cleaning can be provided.

In addition, according to the present invention, a technique for enabling scent emission or deodorization to be achieved at the same timing as a time at which a microorganism sufficiently proliferates and generates a malodor can be provided.

Furthermore, by incorporating the later-described compounds 001 to 118, a fragrance composition, an aromatic product, a laundry care product, a hair care product, a cosmetic, a cleaner or a deodorant, which can emit an aromatic component upon reacting with a hydrolase and make a lingering sent with fresh feeling to last on clothing, hair or skin or which can emit an aromatic component or deodorant component upon reacting with a microorganism and alleviate an unpleasant odor caused by a microorganism, can be provided.

DESCRIPTION OF EMBODIMENTS

The present invention is described in detail below.

Note that in the present invention, the "mass" has the same meaning as "weight".

In the present invention, an alcohol, a phenol or a phenol derivative, which are an aromatic component, can be generated by reacting a fragrance precursor represented by general formula (1) or the later-described compounds 001 to 118 with a hydrolase or microorganism.

[Fragrance Precursor]

The fragrance precursor of the present invention is represented by the following formula (1):

[Chem. 2]

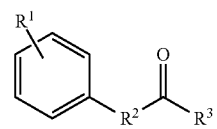

(1)

In formula (1), $R^1$ represents a hydrogen atom, an alkyl group having the carbon number of 1 to 12, a hydroxy group, a methoxy group or an ethoxy group.

The alkyl group having the carbon number of 1 to 12 may be linear or branched and includes, for example, a methyl group, an ethyl group, a n-propyl group, an isopropyl group, a n-butyl group, an isobutyl group, a sec-butyl group, a tert-butyl group, a n-pentyl group, an isopentyl group, a neopentyl group, a hexyl group, a heptyl group, an octyl group, a nonyl group, a decyl group, an undecyl group, and a dodecyl group.

Among these, in view of scent emission performance, $R^1$ is preferably a hydrogen atom, a hydroxy group or a methoxy group, more preferably a hydrogen atom.

In formula (1), $R^2$ represents a single bond, an alkylene group having the carbon number of 1 to 2 which may have a substituent, or a vinylene group which may have a substituent.

The alkylene group having the carbon number of 1 to 2 includes a methylene group and an ethylene group.

The substituent that the alkylene group or vinylene group may have includes, for example, a halogen atom (e.g., fluorine atom, chlorine atom, bromine atom), a hydroxy group, an amino group, a mercapto group, an alkyl group having the carbon number of 1 to 8 (e.g., methyl group, ethyl group, n-propyl group, isopropyl group, tert-butyl group, n-octyl group, 2-ethylhexyl group, cyclohexyl group), an alkenyl group having the carbon number of 2 to 5 (e.g., vinyl group, allyl group, prenyl group, cyclopenten-1-yl group), an alkynyl group having the carbon number of 2 to 3 (e.g., ethynyl group, propargyl group), an aryl group having the carbon number of 6 to 10 (e.g., phenyl group, p-tolyl group, naphthyl group), a heterocyclic group (e.g., 1-pyrazolyl group, 1-imidazolyl group, 2-furyl group, 2-thienyl group, 4-pyrimidinyl group, 2-pyridyl group, 2-benzothiazolyl group), a nitro group, a cyano group, a carbamoyl group, a sulfamoyl group, an acyl group (e.g., formyl group, acetyl group, pivaloyl group, benzoyl group), an alkoxycarbonyl group (e.g., methoxycarbonyl group, ethoxycarbonyl group, tert-butoxycarbonyl group, isobutoxycarbonyl group, an aryloxycarbonyl group (e.g., phenoxycarbonyl group, naphthoxycarbonyl group), a heterocyclic oxycarbonyl group (e.g., 1-pyrazolyloxycarbonyl group, 1-imidazolyloxycarbonyl group, 2-furyloxycarbonyl group, 2-thienyloxycarbonyl group, 2-tetrahydrofuryloxycarbonyl group, 2-morpholyloxycarbonyl group), an imido group (e.g., N-succinimido group, N-phthalimido group), an alkylsulfinyl group (e.g., methylsulfinyl group, ethylsulfinyl group), an arylsulfinyl group (e.g., phenylsulfinyl group), an alkylsulfonyl group (e.g., methylsulfonyl group, ethylsulfonyl group, cyclohexylsulfonyl group), an arylsulfonyl group (e.g., phenylsulfonyl group), a heterocyclic sulfonyl group (e.g., 2-tetrahydropyranylsulfonyl group), a phosphino group (e.g., dimethylphosphino group, diphenylphosphino group), and a phosphinyl group (e.g., phosphinyl group, diethoxyphosphinyl group).

Among these, in view of scent emission performance, $R^2$ is preferably a single bond.

In formula (1), $R^3$ represents a residue resulting from removal of one hydrogen atom of a hydroxy group from a fragrance alcohol having the carbon number of 5 to 20 or a phenol which may have a substituent.

The fragrance alcohol is described here. In the present description, the fragrance alcohol means a hydroxy group-containing scented compound that is used as a fragrance.

Preferable examples of the fragrance alcohol having the carbon number of 5 to 20 include, specifically, an aliphatic alcohol [for example, isoamyl alcohol, isopulegol, 2-ethylhexanol, 1-octanol, 3-octanol, 1-octen-3-ol, 1-decanol, 1-dodecanol, 2,6-nonadienol, nonanol, 2-nonanol, cis-6-nonenol, trans-2, cis-6-nonadienol, cis-3, cis-6-nonadienol, butanol, hexanol, cis-2-hexenol, cis-3-hexenol, cis-4-hexenol, trans-2-hexenol, trans-3-hexenol, 1-undecanol, heptanol, 2-heptanol, 3-methyl-1-pentanol, 2,6-dimethylheptanol, p-tert-butylcyclohexanol, o-tert-butylcyclohexanol, p-isopropylcyclohexylmethanol, ambrinol, 1-(2,2,6-trimethylcyclohexyl)-3-hexanol, 9-decenol, 4-methyl-3-decen-5-ol, methyltrimethylcyclopentenylbutenol, ethyltrimethylcyclopentenylbutenol, 3-methyl-5-(2,2,3-trimethylcyclopent-3-en-1-yl)-pentan-2-ol, 3,3-dimethyl-5-(2,2,3-trimethyl-3-cyclopenten-1-yl)-4-pentan-2-ol, 3-methyl-5-(2,2,3-trimethyl-3-cyclopenten-1-yl)-penten-2-ol, p-isopropylcyclohexanol, 2,4-dimethyl-3-cyclohexene-1-methanol, 1-(2-tert-butylcyclohexyl)-2-butanol, {1-methyl-2-[(1,2,2-trimethylbicyclo[3.1.0]hex-3-yl)methyl]cyclopropyl}methanol, 1-(4-isopropyl-cyclohexyl)ethanol, 2-{(1,7,7-trimethylbicyclo[2.2.1]-2-heptyl)oxy}-1-ethanol, 4-cyclohexyl-2-methylbutan-2-ol, (1R,2S)-2-pentylcyclopentan-1-ol, etc.], a terpene alcohol [for example, carveol, borneol, isoborneol, piperitol, geraniol, tetrahydrogeraniol, α- or β-fenchyl alcohol, 2-methylfenchyl alcohol, α- or p-santalol, citronellol, 4-thujanol, terpineol, 4-terpineol, dihydroterpineol, nerol, myrcenol, myrtenol, mugol, tetrahydromugol, menthol, dihydromyrcenol, tetrahydromyrcenol, lavandulol, nopol, nerolidol, hydroxycitronerol, farnesol, perilla alcohol, rhodinol, linalool, dihydrolinalool, tetrahydrolinalool, ethyllinalool, isopulegol, dihydrofarnesol, isocamphylcyclohexanol, vetiverol, cedrol, patchouli alcohol, etc.], an aromatic alcohol [for example, anise alcohol, α-amylcinnamic alcohol, 3-methyl-5-phenylpentanol-1, isopropylbenzylcarbinol, carvacrol, cuminic alcohol, dimethylbenzylcarbinol, dimethylphenylethylcarbinol, cinnamic alcohol, phenylallyl alcohol, phenylethylcarbinol, phenylethyl alcohol, 3-phenylpropyl alcohol, benzyl alcohol, 2-methyl-4-phenylpentanol, 2,2-dimethyl-3-(3-methylphenyl)propanol, 3-methyl-5-phenylpentanol-1,2-methyl-5-phenylpentan-1-ol, 4-methyl-2(2-methylpropyl)tetrahydro-2H-4-pyranol, etc.], eugenol, isoeugenol, dihydroeugenol, 2-methoxy-4-vinylphenol, thymol, hinokithiol, guaiacol, chavicol, salicylaldehyde, hydroxycitronellal, hydroxycitronellal dimethyl acetal, hydroxycitronellal diethyl acetal, vanillin propylene glycol acetal, ethylvanillin, vanillin, vanitrope, 4-methyl-2-ethoxyphenol, methyl lavender ketone, furaneol, raspberry ketone, maltol, ethylmaltol, zingerone, methyl salicylate, ethyl salicylate, butyl salicylate, isobutyl salicylate, amyl salicylate, isoamyl salicylate, prenyl salicylate, hexyl salicylate, cis-3-hexenyl salicylate, cyclohexyl salicylate, benzyl salicylate, phenylethyl salicylate, isopropoxyethyl salicylate, ethyl lactate, and methyl atrarate.

The phenol which may have a substituent includes, for example, the following compounds.

[Chem. 3]

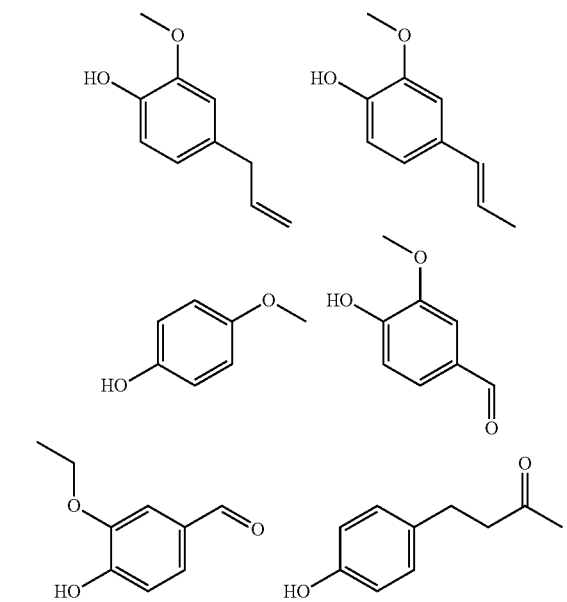

Among these, in view of aroma, $R^3$ is preferably a residue resulting from removal of one hydrogen atom of a hydroxy group from a fragrance alcohol having the carbon number of 6 to 15.

Specific Examples of Compound Represented by General Formula (1)

Specific examples of the compound represented by general formula (1) of the present invention include the later-described compounds 001 to 118 and the following compound.

[Chem. 4]

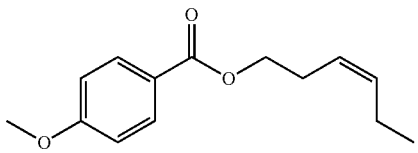

In addition, specific examples of the compound represented by general formula (1) of the present invention include the following compounds synthesized in Examples later. In the following compounds, nPr stands for a normal-propyl group and Me stands for a methyl group.

[Chem. 5]

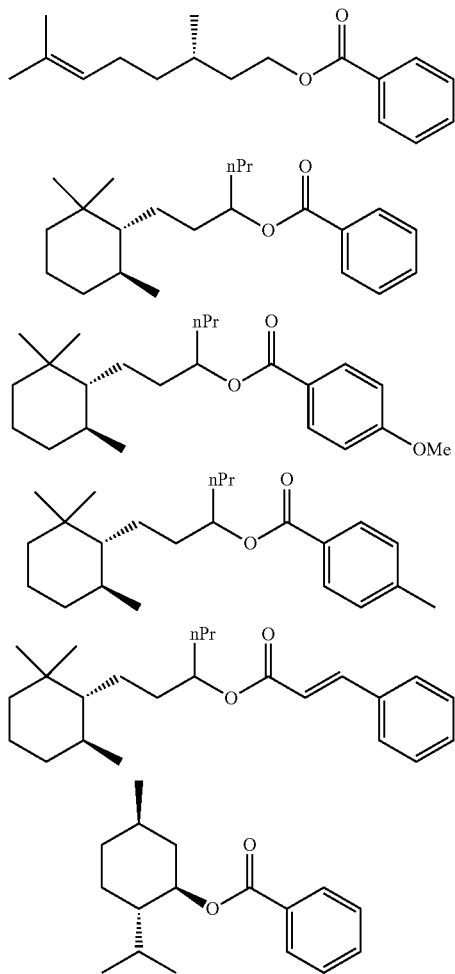

[Chem. 6]

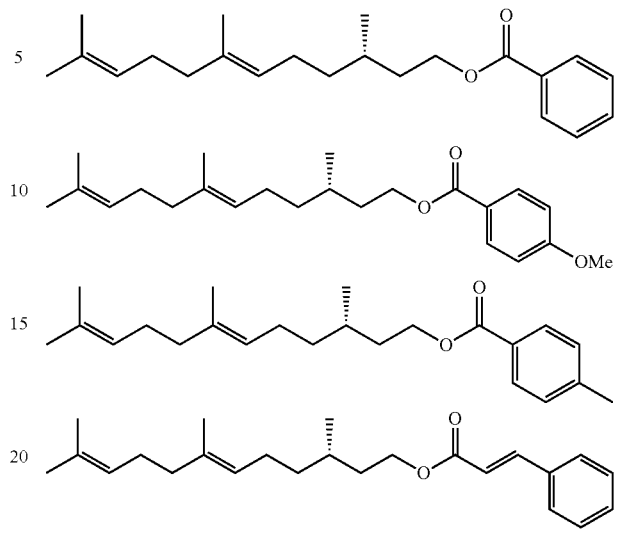

[Chem. 7]

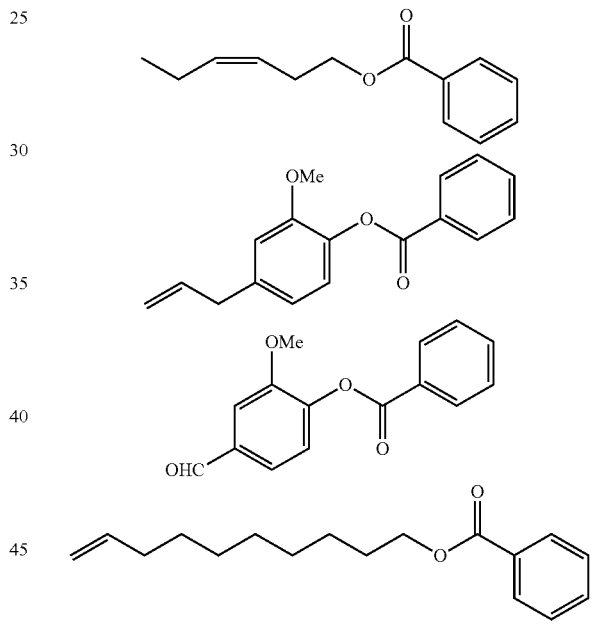

Furthermore, specific examples of the compound represented by general formula (1) of the present invention include geranyl benzoate, geranyl phenylacetate, geranyl salicylate, phenylethyl benzoate, phenylethyl phenylacetate, phenylethyl salicylate, phenylethyl cinnamate, citronellyl benzoate, citronellyl phenylacetate, citronellyl salicylate, linalyl benzoate, linalyl cinnamate, linalyl phenylacetate, linalyl salicylate, cinnamyl benzoate, cinnamyl cinnamate, eugenyl benzoate, eugenyl phenylacetate, eugenyl salicylate, isoeugenyl benzoate, isoeugenyl phenylacetate, isoeugenyl salicylate, menthyl benzoate, menthyl phenylacetate, menthyl salicylate, rhodinyl benzoate, rhodinyl phenylacetate, neryl benzoate, neryl phenylacetate, neryl salicylate, terpinyl benzoate, anisyl benzoate, anisyl phenylacetate, anisyl salicylate, cis-3-hexenyl benzoate, cis-3-hexenyl phenylacetate, cis-3-hexenyl salicylate, vanillyl benzoate, vanillyl phenylacetate, and 9-decenyl benzoate.

(Synthesis Method of Compound Represented by General Formula (1))

The compound represented by general formula (1) of the present invention can be easily synthesized by a known method. The compound represented by general formula (1) can be synthesized, for example, in accordance with the method described in J. Org. Chem. 51.1006 (1986) or J. Org. Chem. 46.5252 (1981).

Out of the compounds represented by general formula (1) of the present invention, a synthesis method of 1-((1R,6S)-2,2,6-trimethylcyclohexyl)-3-hexanyl benzoate represented by the following formula (1a) is shown in the scheme below.

[Chem. 8]

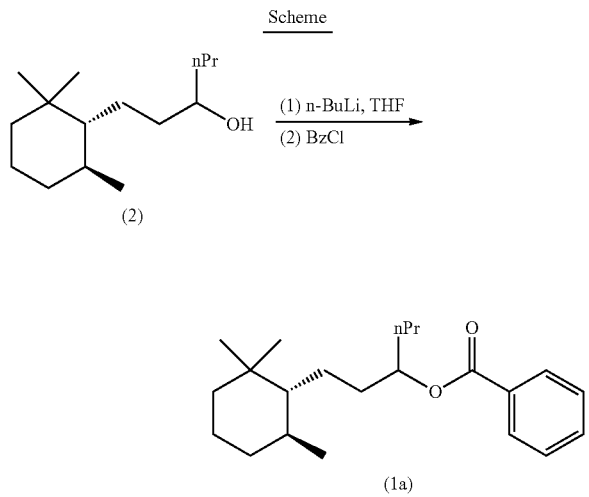

As for the synthesis of the compound represented by formula (1a), the compound can be prepared by lithiating a hydroxyl group of Ambestol (compound represented by formula (2)) with butyllithium in a tetrahydrofuran solvent, followed by a reaction with benzoyl chloride. The acylating agent used is preferably benzoyl chloride or benzoic anhydride, etc. The compound represented by formula (1a) obtained as above can be isolated and purified, for example, by an operation usually employed, such as extraction, distillation, recrystallization and various chromatographies.

[Method for Releasing Fragrance Alcohol, Phenol or Phenol Derivative]

A fragrance alcohol, a phenol or a phenol derivative, which are an aromatic component, can be released by reacting the compound represented by general formula (1) with a hydrolase or microorganism.

The method for reacting the compound represented by general formula (1) with a hydrolase includes, for example, a method of mixing the compound represented by general formula (1) with a hydrolase-containing aqueous solution.

The content of the hydrolase in the hydrolase-containing aqueous solution is usually from 0.001 to 50 mass %, preferably from 0.01 to 10 mass %.

The mass of the compound represented by general formula (1) used at the time of mixing is usually from 0.001 to 10,000 mg, preferably from 0.01 to 1,000 mg, per 1 g of the hydrolase-containing aqueous solution.

When the compound represented by general formula (1) reacts with a hydrolase, an ester bond in the compound represented by general formula (1) is hydrolyzed, and a fragrance alcohol, a phenol or a phenol derivative is released.

The hydrolase includes lipase, protease, amylase, glycosidase, esterase, etc., and among these, in view of the hydrolysis rate, lipase is preferred.

The lipase is not limited to a particular one and, as long as it is an enzyme that breaks down fat, may be a naturally occurring material or a formulated commercial product.

The method for reacting the compound represented by general formula (1) with a microorganism includes, for example, a method of mixing the compound represented by general formula (1) with a microbial culture.

The method for culturing a microorganism is not particularly limited, and a known method may be used.

The amount of bacteria in the microbial culture is usually from $10^3$ to $10^{12}$ cfu/mL, preferably from 106 to $10^{10}$ cfu/mL.

In addition, the mass of the compound represented by general formula (1) used at the time of mixing is usually from 0.01 to 10 mg, preferably from 0.1 to 5 mg, per 1 mL of the microbial culture.

It is considered that when the compound represented by general formula (1) reacts with a microorganism, the compound is ingested inside the microorganism and metabolized, or an ester bond in the compound is hydrolyzed by the action of an enzyme group secreted outside the microorganism, as a result, a fragrance alcohol, a phenol or a phenol derivative is released.

The microorganism includes *Staphylococcus* bacteria, *Corynebacterium* bacteria, *Propionibacterium* bacteria, *Pseudomonas* bacteria, *Bacillus* bacteria, *Moraxella* bacteria, *Malassezia* fungi, etc.

More specifically, the microorganism includes *Staphylococcus aureus, Staphylococcus epidermidis, Corynebacterium xerosis, Propionibacterium acnes, Pseudomonas aeruginosa, Bacillus subtilis, Moraxella osloensis, Malassezia furfur*, etc.

[Compounds 001 to 118]

The compound of the present invention is at least one novel compound selected from the group consisting of compounds 001 to 118 shown in Tables 1 to 12 below (hereinafter, sometimes simply referred to as "compound of the present invention").

TABLE 1

| Compound 001 | 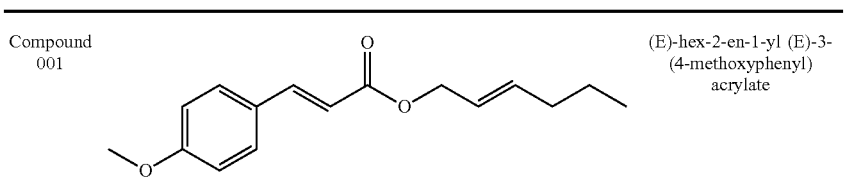 | (E)-hex-2-en-1-yl (E)-3-(4-methoxyphenyl)acrylate |
|---|---|---|

TABLE 1-continued

| Compound | Structure | Name |
|---|---|---|
| Compound 002 | 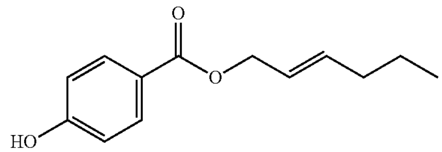 [SMILES: CCC/C=C/COC(=O)c1ccc(O)cc1] | (E)-hex-2-en-1-yl 4-hydroxybenzoate |
| Compound 003 | 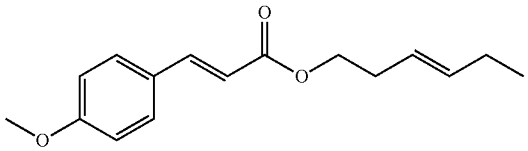 [SMILES: CC/C=C/CCOC(=O)/C=C/c1ccc(OC)cc1] | (E)-hex-3-en-1-yl (E)-3-(4-methoxyphenyl) acrylate |
| Compound 004 | 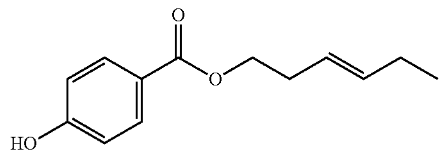 [SMILES: CC/C=C/CCOC(=O)c1ccc(O)cc1] | (E)-hex-3-en-1-yl 4-hydroxybenzoate |
| Compound 005 | 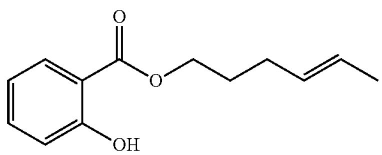 [SMILES: C/C=C/CCCOC(=O)c1ccccc1O] | (E)-hex-4-en-1-yl 2-hydroxybenzoate |
| Compound 006 | 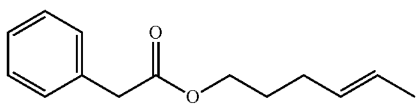 [SMILES: C/C=C/CCCOC(=O)Cc1ccccc1] | (E)-hex-4-en-1-yl 2-phenylacetate |
| Compound 007 | 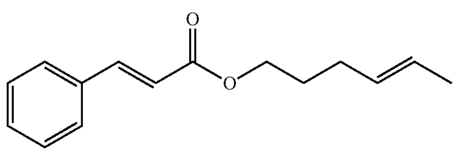 [SMILES: C/C=C/CCCOC(=O)/C=C/c1ccccc1] | (E)-hex-4-en-1-yl cinnamate |
| Compound 008 | 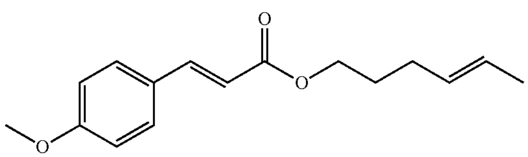 [SMILES: C/C=C/CCCOC(=O)/C=C/c1ccc(OC)cc1] | (E)-hex-4-en-1-yl (E)-3-(4-methoxyphenyl) acrylate |
| Compound 009 | 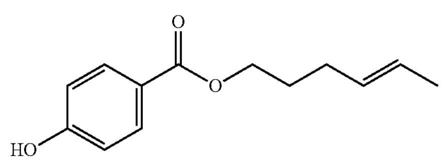 [SMILES: C/C=C/CCCOC(=O)c1ccc(O)cc1] | (E)-hex-4-en-1-yl 4-hydroxybenzoate |
| Compound 010 | 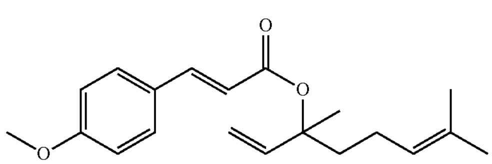 [SMILES: C=CC(C)(CCC=C(C)C)OC(=O)/C=C/c1ccc(OC)cc1] | 3,7-dimethylocta-1,6-dien-3-yl (E)-3-(4-methoxyphenyl) acrylate |
| Compound 011 | 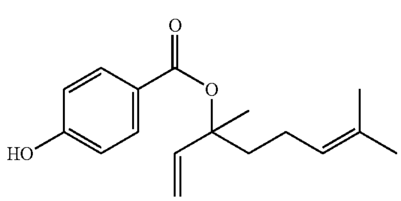 [SMILES: C=CC(C)(CCC=C(C)C)OC(=O)c1ccc(O)cc1] | 3,7-dimethylocta-1,6-dien-3-yl 4-hydroxybenzoate |

TABLE 2

| Compound 012 | | 3,7-dimethyloct-6-en-1-yl (E)-3-(4-methoxyphenyl) acrylate |
| Compound 013 | | 4-allyl-2-methoxyphenyl 4-hydroxybenzoate |
| Compound 014 | | (E)-2-methoxy-4-(prop-1-en-1-yl)phenyl 2-hydroxybenzoate |
| Compound 015 | | (E)-2-methoxy-4-(prop-1-en-1-yl) phenyl 4-methoxybenzoate |
| Compound 016 | | 2-methoxy-4-((E)-prop-1-en-1-yl) phenyl (E)-3-(4-methoxyphenyl) acrylate |
| Compound 017 | | (E)-2-methoxy-4-(prop-1-en-1-yl) phenyl 4-hydroxybenzoate |
| Compound 018 | | 2,6-dimethyloct-7-en-2-yl benzoate |

TABLE 2-continued

| Compound 019 | | 2,6-dimethyloct-7-en-2-yl 2-hydroxybenzoate |
| Compound 020 | | 2,6-dimethyloct-7-en-2-yl 2-phenylacetate |

TABLE 3

| Compound 021 | | 2,6-dimethyloct-7-en-2-yl cinnamate |
| Compound 022 | | 2,6-dimethyloct-7-en-2-yl 4-methoxybenzoate |
| Compound 023 | | 2,6-dimethyloct-7-en-2-yl (E)-3-(4-methoxyphenyl)acrylate |
| Compound 024 | | 2,6-dimethyloct-7-en-2-yl 4-hydroxybenzoate |
| Compound 025 | | 3,7-dimethyloctan-3-yl benzoate |
| Compound 026 | | 3,7-dimethyloctan-3-yl 2-hydroxybenzoate |
| Compound 027 | | 3,7-dimethyloctan-3-yl 2-phenylacetate |

TABLE 3-continued

| Compound | | |
|---|---|---|
| Compound 028 | 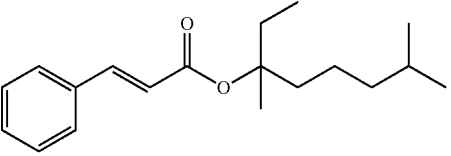 [SMILES: CCC(C)(CCCC(C)C)OC(=O)/C=C/c1ccccc1] | 3,7-dimethyloctan-3-yl cinnamate |
| Compound 029 | 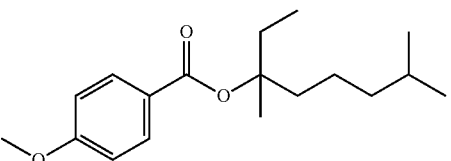 | 3,7-dimethyloctan-3-yl 4-methoxybenzoate |
| Compound 030 | 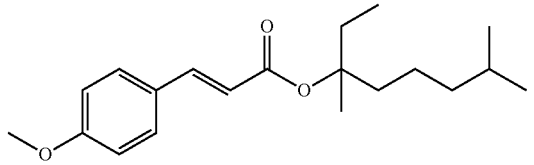 [SMILES: CCC(C)(CCCC(C)C)OC(=O)/C=C/c1ccc(OC)cc1] | 3,7-dimethyloctan-3-yl (E)-3-(4-methoxyphenyl)acrylate |
| Compound 031 | 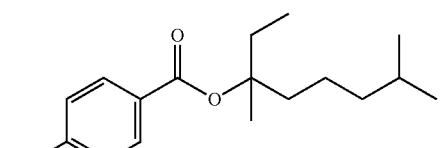 | 3,7-dimethyloctan-3-yl 4-hydroxybenzoate |

TABLE 4

| Compound | | |
|---|---|---|
| Compound 032 | 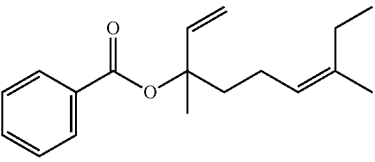 [SMILES: C=CC(C)(CC/C=C(/C)CC)OC(=O)c1ccccc1] | (Z)-3,7-dimethylnona-1,6-dien-3-yl benzoate |
| Compound 033 | 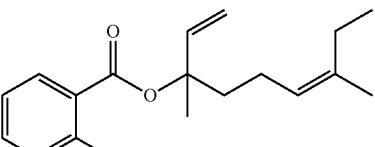 | (Z)-3,7-dimethylnona-1,6-dien-3-yl 2-hydroxybenzoate |
| Compound 034 | 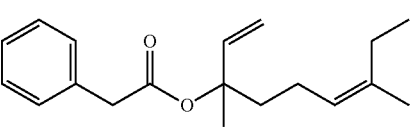 [SMILES: C=CC(C)(CC/C=C(/C)CC)OC(=O)Cc1ccccc1] | (Z)-3,7-dimethylnona-1,6-dien-3-yl 2-phenylacetate |
| Compound 035 | 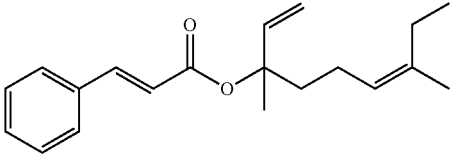 [SMILES: C=CC(C)(CC/C=C(/C)CC)OC(=O)/C=C/c1ccccc1] | (Z)-3,7-dimethylnona-1,6-dien-3-yl cinnamate |
| Compound 036 | 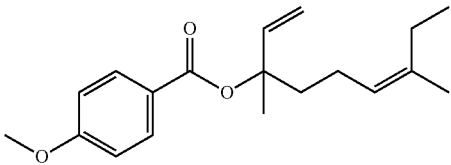 [SMILES: C=CC(C)(CC/C=C(/C)CC)OC(=O)c1ccc(OC)cc1] | ((Z)-3,7-dimethylnona-1,6-dien-3-yl 4-methoxybenzoate |

TABLE 4-continued

| Compound 037 | (structure) | (Z)-3,7-dimethylnona-1,6-dien-3-yl (E)-3-(4-methoxyphenyl) acrylate |
| Compound 038 | (structure) | (Z)-3,7-dimethylnona-1,6-dien-3-yl 4-hydroxybenzoate |
| Compound 039 | (structure) | 2-(4-methylcyclohex-3-en-1-yl) propan-2-yl 4-methoxybenzoate |
| Compound 040 | (structure) | 2-(4-methylcyclohex-3-en-1-yl) propan-2-yl (E)-3-(4-methoxyphenyl) acrylate |
| Compound 041 | (structure) | 1-methyl-4-(prop-1-en-2-yl) cyclohexyl 2-hydroxybenzoate |
| Compound 042 | (structure) | 1-methyl-4-(prop-1-en-2-yl) cyclohexyl 2-phenylacetate |

TABLE 5

| Compound 043 | (structure) | 1-methyl-4-(prop-1-en-2-yl)cyclohexyl cinnamate |
| Compound 044 | (structure) | 1-methyl-4-(prop-1-en-2-y) cyclohexyl 4-methoxybenzoate |

TABLE 5-continued

| Compound 045 | 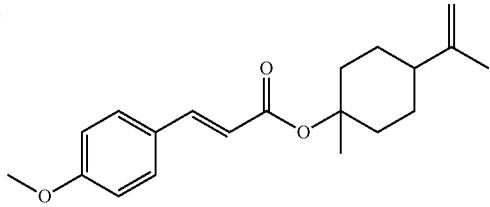 [SMILES: C=C(C)C1CCC(C)(OC(=O)/C=C/c2ccc(OC)cc2)CC1] | 1-methyl-4-(prop-1-en-2-yl)cyclohexyl (E)-3-(4-methoxyphenyl)acrylate |
| Compound 046 | 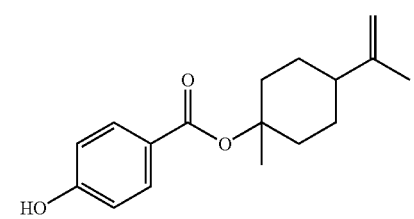 [SMILES: C=C(C)C1CCC(C)(OC(=O)c2ccc(O)cc2)CC1] | 1-methyl-4-(prop-1-en-2-yl)cyclohexyl 4-hydroxybenzoate |
| Compound 047 | 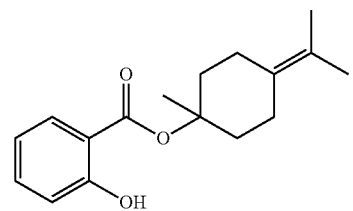 [SMILES: CC(C)=C1CCC(C)(OC(=O)c2ccccc2O)CC1] | 1-methyl-4-(propan-2-ylidene)cyclohexyl 2-hydroxybenzoate |
| Compound 048 | 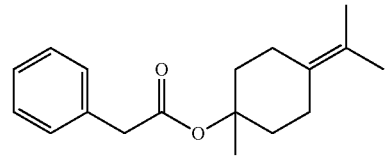 [SMILES: CC(C)=C1CCC(C)(OC(=O)Cc2ccccc2)CC1] | 1-methyl-4-(propan-2-ylidene)cyclohexyl 2-phenylacetate |
| Compound 049 | 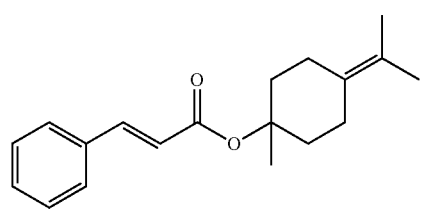 [SMILES: CC(C)=C1CCC(C)(OC(=O)/C=C/c2ccccc2)CC1] | 1-methyl-4-(propan-2-ylidene)cyclohexyl cinnamate |
| Compound 050 | 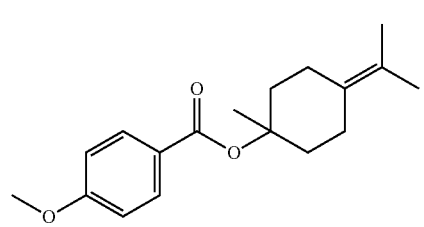 [SMILES: COc1ccc(C(=O)OC2(C)CCC(=C(C)C)CC2)cc1] | 1-methyl-4-(propan-2-ylidene)cyclohexyl 4-methoxybenzoate |
| Compound 051 | 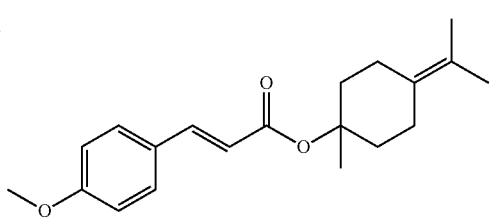 [SMILES: COc1ccc(/C=C/C(=O)OC2(C)CCC(=C(C)C)CC2)cc1] | 1-methyl-4-(propan-2-ylidene)cyclohexyl (E)-3-(4-methoxyphenyl)acrylate |

TABLE 5-continued

| Compound 052 | [structure] | 1-methyl-4-(propan-2-ylidene)cyclohexyl 4-hydroxybenzoate |
| Compound 053 | [structure] | 1-isopropyl-4-methylcyclohex-3-en-1-yl 2-hydroxybenzoate |

TABLE 6

| Compound 054 | [structure] | 1-isopropyl-4-methylcyclohex-3-en-1-yl 2-phenylacetate |
| Compound 055 | [structure] | 1-isopropyl-4-methylcyclohex-3-en-1-yl (E)-3-(4-methoxyphenyl)acrylate |
| Compound 056 | [structure] | 1-isopropyl-4-methylcyclohex-3-en-1-yl 4-hydroxybenzoate |
| Compound 057 | [structure] | 2,6-dimethylheptan-2-yl benzoate |
| Compound 058 | [structure] | 2,6-dimethylheptan-2-yl 2-hydroxybenzoate |
| Compound 059 | [structure] | 2,6-dimethylheptan-2-yl 2-phenylacetate |

TABLE 6-continued

| Compound 060 | [structure] | 2,6-dimethylheptan-2-yl cinnamate |
| Compound 061 | [structure] | 2,6-dimethylheptan-2-yl 4-methoxybenzoate |
| Compound 062 | [structure] | 2,6-dimethylheptan-2-yl (E)-3-(4-methoxyphenyl)acrylate |
| Compound 063 | [structure] | 2,6-dimethylheptan-2-yl 4-hydroxybenzoate |
| Compound 064 | [structure] | 2,6-dimethyl-8-oxooctan-2-yl benzoate |

TABLE 7

| Compound 065 | [structure] | 2,6-dimethyl-8-oxooctan-2-yl 2-hydroxybenzoate |
| Compound 066 | [structure] | (2,6-dimethyl-8-oxooctan-2-yl 2-phenylacetate |
| Compound 067 | [structure] | 2,6-dimethyl-8-oxooctan-2-yl cinnamate |
| Compound 068 | [structure] | 2,6-dimethyl-8-oxooctan-2-yl 4-methoxybenzoate |

TABLE 7-continued

| Compound 069 | 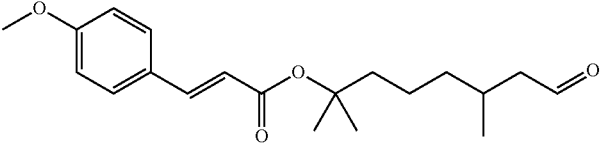 [SMILES: COc1ccc(/C=C/C(=O)OC(C)(C)CCCC(C)CC=O)cc1] | 2,6-dimethyl-8-oxooctan-2-yl (E)-3-(4-methoxyphenyl)acrylate |
| Compound 070 | 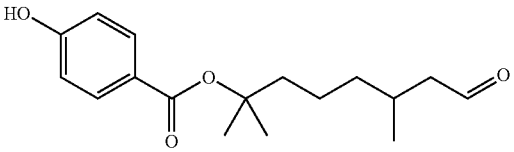 [SMILES: CC(CC=O)CCCC(C)(C)OC(=O)c1ccc(O)cc1] | 2,6-dimethyl-8-oxooctan-2-yl 4-hydroxybenzoate |
| Compound 071 | 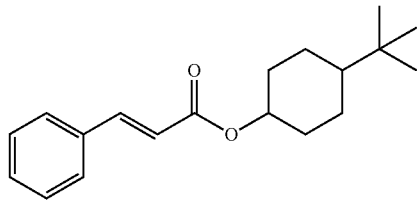 [SMILES: CC(C)(C)C1CCC(OC(=O)/C=C/c2ccccc2)CC1] | 4-(tert-butyl) cyclohexyl cinnamate |
| Compound 072 | 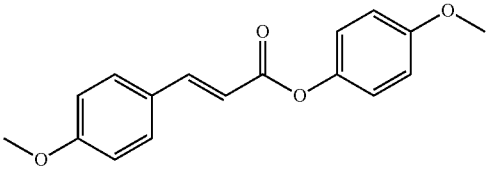 | 4-methoxyphenyl (E)-3-(4-methoxyphenyl) acrylate |
| Compound 073 | 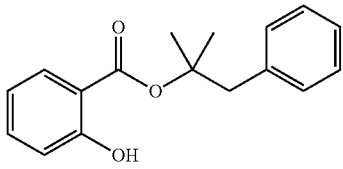 [SMILES: CC(C)(Cc1ccccc1)OC(=O)c1ccccc1O] | 2-methyl-1-phenylpropan-2-yl 2-hydroxybenzoate |
| Compound 074 | 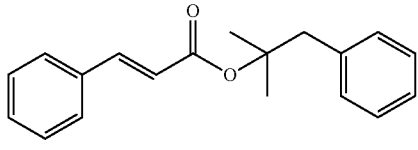 [SMILES: CC(C)(Cc1ccccc1)OC(=O)/C=C/c1ccccc1] | 2-methyl-1-phenylpropan-2-yl cinnamate |
| Compound 075 | 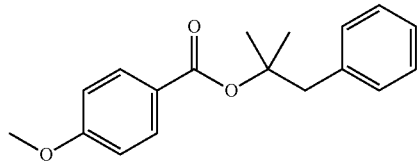 [SMILES: COc1ccc(C(=O)OC(C)(C)Cc2ccccc2)cc1] | 2-methyl-1-phenylpropan-2-yl 4-methoxybenzoate |

TABLE 8

| Compound 076 | 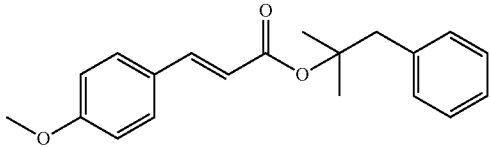 [SMILES: COc1ccc(/C=C/C(=O)OC(C)(C)Cc2ccccc2)cc1] | 2-methyl-1-phenylpropan-2-yl (E)-3-(4-methoxyphenyl) acrylate |

TABLE 8-continued

| Compound 077 | 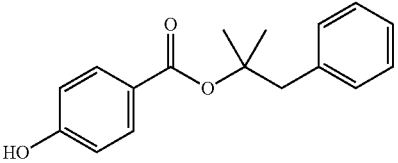 [SMILES: CC(C)(Cc1ccccc1)OC(=O)c1ccc(O)cc1] | 2-methyl-1-phenylpropan-2-yl 4-hydroxybenzoate |
| Compound 078 | 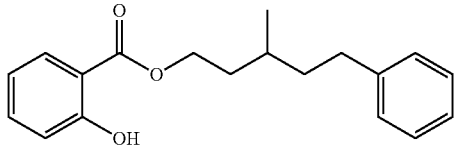 [SMILES: CC(CCOC(=O)c1ccccc1O)CCc1ccccc1] | 3-methyl-5-phenylpentyl 2-hydroxybenzoate |
| Compound 079 | 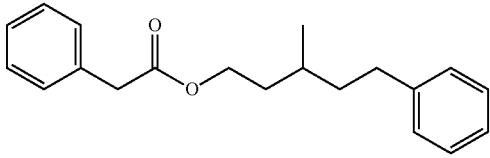 [SMILES: CC(CCOC(=O)Cc1ccccc1)CCc1ccccc1] | 3-methyl-5-phenylpentyl 2-phenylacetate |
| Compound 080 | 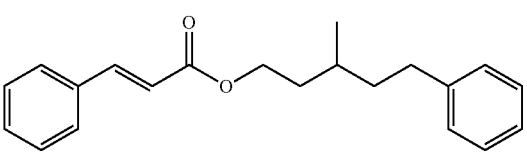 [SMILES: CC(CCOC(=O)/C=C/c1ccccc1)CCc1ccccc1] | 3-methyl-5-phenylpentyl cinnamate |
| Compound 081 | 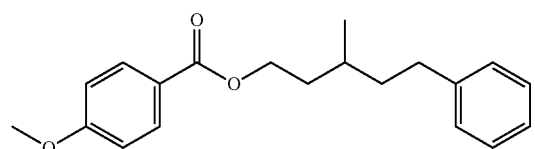 | 3-methyl-5-phenyl-pentyl 4-methoxybenzoate |
| Compound 082 | 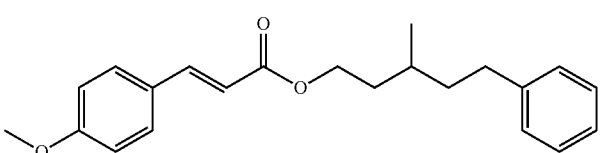 | 3-methyl-5-phenyl-pentyl (E)-3-(4-methoxyphenyl)acrylate |
| Compound 083 | 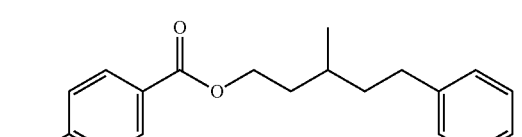 | 3-methyl-5-phenylpentyl 4-hydroxybenzoate |
| Compound 084 | 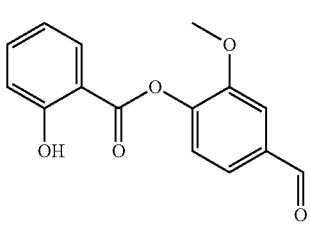 [SMILES: COc1cc(C=O)ccc1OC(=O)c1ccccc1O] | 4-formyl-2-methoxyphenyl 2-hydroxybenzoate |
| Compound 085 | 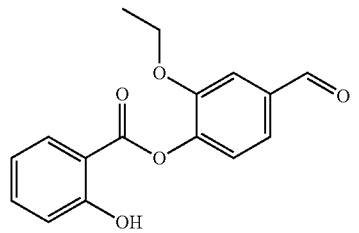 [SMILES: CCOc1cc(C=O)ccc1OC(=O)c1ccccc1O] | 2-ethoxy-4-formylphenyl 2-hydroxybenzoate |

TABLE 9
| Compound 086 | 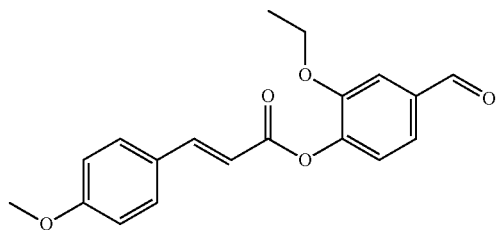 [SMILES: CCOc1cc(C=O)ccc1OC(=O)/C=C/c1ccc(OC)cc1] | 2-ethoxy-4-formylphenyl (E)-3-(4-methoxyphenyl) acrylate |
| Compound 087 | 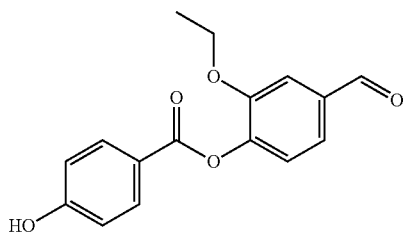 [SMILES: CCOc1cc(C=O)ccc1OC(=O)c1ccc(O)cc1] | 2-ethoxy-4-formylphenyl 4-hydroxybenzoate |
| Compound 088 | 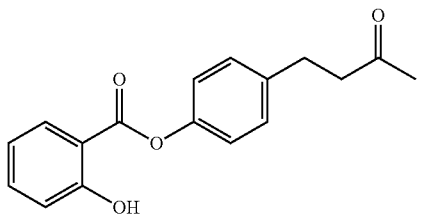 [SMILES: CC(=O)CCc1ccc(OC(=O)c2ccccc2O)cc1] | 4-(3-oxobutyl)phenyl 2-hydroxybenzoate |
| Compound 089 | 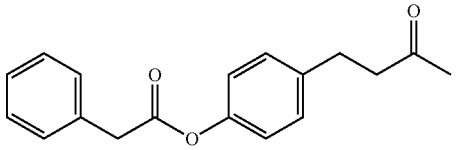 [SMILES: CC(=O)CCc1ccc(OC(=O)Cc2ccccc2)cc1] | 4-(3-oxobutyl)phenyl 2-phenylacetate |
| Compound 090 | 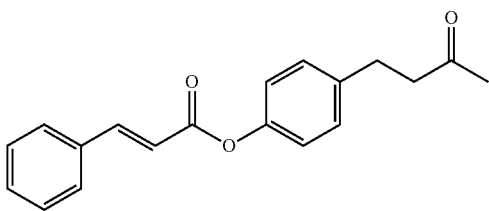 [SMILES: CC(=O)CCc1ccc(OC(=O)/C=C/c2ccccc2)cc1] | 4-(3-oxobutyl)phenyl cinnamate |
| Compound 091 | 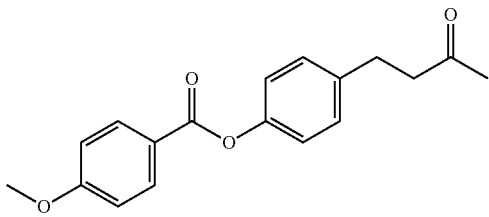 [SMILES: COc1ccc(C(=O)Oc2ccc(CCC(C)=O)cc2)cc1] | 4-(3-oxobutyl)phenyl 4-methoxybenzoate |
| Compound 092 | 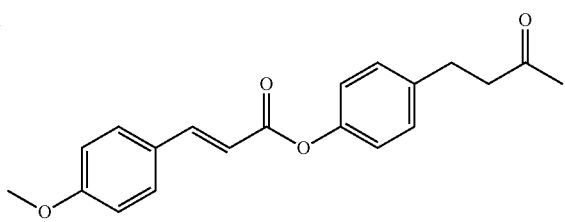 [SMILES: COc1ccc(/C=C/C(=O)Oc2ccc(CCC(C)=O)cc2)cc1] | 4-(3-oxobutyl)phenyl (E)-3-(4-methoxyphenyl) acrylate |

TABLE 9-continued

| Compound 093 | | 4-(3-oxobutylphenyl 4-hydroxybenzoate |
| --- | --- | --- |
| Compound 094 | | 1,3,3-trimethylbicyclo[2.2.1]heptan-2-yl 2-hydroxybenzoate |

TABLE 10

| Compound 095 | | 1,3,3-trimethyl-bicyclo[2.2.1]heptan-2-yl 2-phenylacetate |
| --- | --- | --- |
| Compound 096 | | 1,3,3-trimethyl-bicyclo[2.2.1]heptan-2-yl cinnamate |
| Compound 097 | | 1,3,3-trimethyl-bicyclo[2.2.1]heptan-2-yl 4-methoxybenzoate |
| Compound 098 | | 1,3,3-trimethyl-bicyclo[2.2.1]heptan-2-yl (E)-3-(4-methoxyphenyl)acrylate |
| Compound 099 | | 1,3,3-trimethyl-bicyclo[2.2.1]heptan-2-yl 4-hydroxybenzoate |
| Compound 100 | | 1-((1R,6S)-2,2,6-trimethylcyclohexyl)hexan-3-yl benzoate |

TABLE 10-continued

| Compound 101 | [structure] | 1-((1R,6S)-2,2,6-trimethylcyclohexyl)hexan-3-yl 2-hydroxybenzoate |
| --- | --- | --- |
| Compound 102 | [structure] | 1-((1R,6S)-2,2,6-trimethylcyclohexyl)hexan-3-yl 2-phenylacetate |
| Compound 103 | [structure] | 1-((1R,6S)-2,2,6-trimethylcyclohexyl)hexan-3-yl cinnamate |
| Compound 104 | [structure] | 1-((1R,6S)-2,2,6-trimethylcyclohexyl)hexan-3-yl 4-methoxybenzoate |

TABLE 11

| Compound 105 | [structure] | 1-((1R,6S)-2,2,6-trimethylcyclohexyl)hexan-3-yl (E)-3-(4-methoxyphenyl)acrylate |
| --- | --- | --- |
| Compound 106 | [structure] | 1-((1R,6S)-2,2,6-trimethylcyclohexyl)hexan-3-yl 4-hydroxybenzoate |

TABLE 11-continued

| Compound | Structure | Name |
|---|---|---|
| Compound 107 | 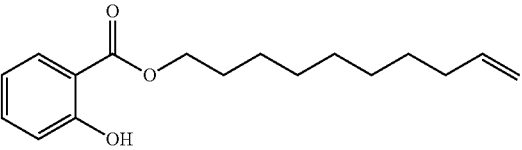 [SMILES: C=CCCCCCCCCOC(=O)c1ccccc1O] | dec-9-en-1-yl 2-hydroxybenzoate |
| Compound 108 | 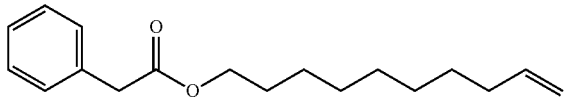 [SMILES: C=CCCCCCCCCOC(=O)Cc1ccccc1] | dec-9-en-1-yl 2-phenylacetate |
| Compound 109 | 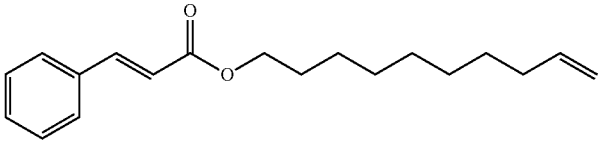 [SMILES: C=CCCCCCCCCOC(=O)/C=C/c1ccccc1] | dec-9-en-1-yl cinnamate |
| Compound 110 | 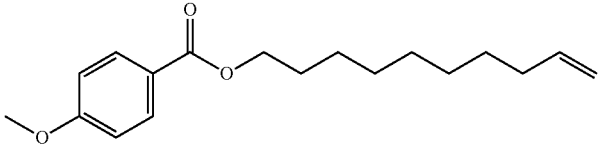 [SMILES: C=CCCCCCCCCOC(=O)c1ccc(OC)cc1] | dec-9-en-1-yl 4-methoxybenzoate |
| Compound 111 | 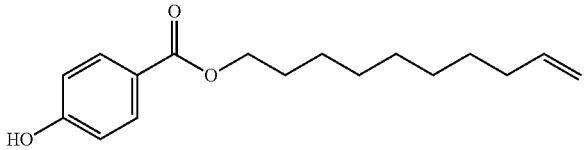 [SMILES: C=CCCCCCCCCOC(=O)c1ccc(O)cc1] | dec-9-en-1-yl 4-hydroxybenzoate |
| Compound 112 | 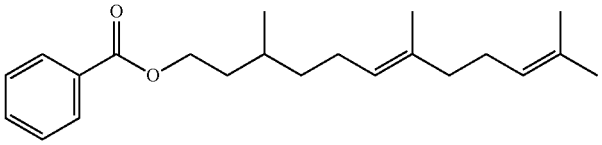 [SMILES: CC(C)=CCC/C(C)=C/CCC(C)CCOC(=O)c1ccccc1] | (E)-3,7,11-trimethyl-dodeca-6,10-dien-1-yl benzoate |
| Compound 113 | 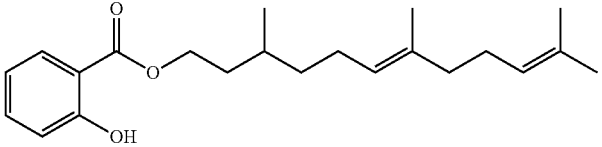 [SMILES: CC(C)=CCC/C(C)=C/CCC(C)CCOC(=O)c1ccccc1O] | (E)-3,7,11-trimethyl-dodeca-6,10-dien-1-yl 2-hydroxybenzoate |
| Compound 114 | 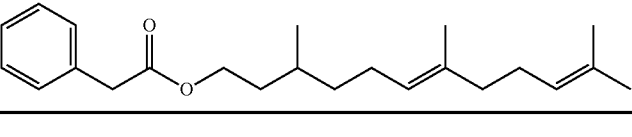 | (E)-3,7,11-trimethyl-dodeca-6,10-dien-1-yl 2-phenylacetate |

TABLE 12

| Compound | Structure | Name |
|---|---|---|
| Compound 115 | 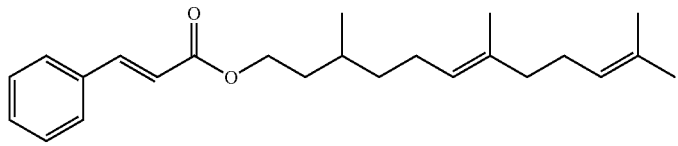 [SMILES: CC(C)=CCC/C(C)=C/CCC(C)CCOC(=O)/C=C/c1ccccc1] | (E)-3,7,11-trimethyldodeca-6,10-dien-1-yl cinnamate |
| Compound 116 | 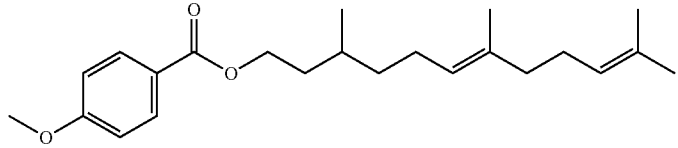 [SMILES: COc1ccc(C(=O)OCCC(C)CC/C=C(\C)CCC=C(C)C)cc1] | (E)-3,7,11-trimethyldodeca-6,10-dien-1-yl 4-methoxybenzoate |

TABLE 12-continued

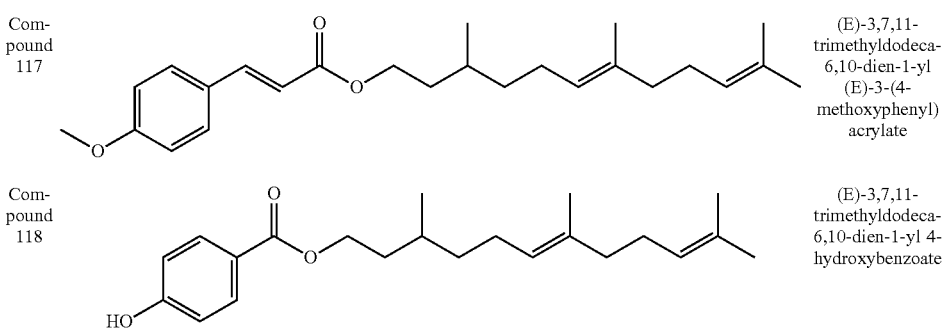

[Fragrance Composition]

The fragrance composition of the present invention contains the compound of the present invention. The compound of the present invention may be used individually or in combination of two or more kinds and may also be used in appropriate combination with known fragrance components.

Known fragrance components include, for example, natural essential oils such as lemon oil, orange oil, lime oil, bergamot oil, lavandin oil, lavender oil, geranium oil, rose oil and sandalwood oil, hydrocarbons such as α-pinene, β-pinene, limonene, p-cymene and thujone, aliphatic alcohols such as octanol and p-tert-butylcyclohexanol, terpene-based alcohols such as menthol, citronellol and geraniol, aromatic alcohols such as benzyl alcohol and phenylethyl alcohol, aliphatic aldehydes, terpene-based aldehydes, aromatic aldehydes, acetals, chain ketones, cyclic ketones such as damascone, β-ionone and Methylionone, terpene-based ketones such as carvone, menthone, isomenthone and camphor, aromatic ketones such as acetophenone and raspberry ketone, ethers such as dibenzyl ether, oxides such as linalool oxide and rose oxide, musks such as cyclopentadecanolide and cyclohexadecanolide, lactones such as γ-nonalactone, γ-undecalactone and coumarin, aliphatic esters such as acetic acid ester and propionic acid ester, and aromatic esters such as benzoic acid ester and phenylacetic acid ester.

The fragrance composition of the present invention may contain a solvent, for example, ethanol, isopropyl alcohol, ethylene glycol, propylene glycol, dipropylene glycol, butylene glycol, pentylene glycol, hexylene glycol, polyethylene glycol, diethyl phthalate, isopropyl myristate, triethyl citrate, benzyl benzoate, glycerin, triacetin, benzyl alcohol, paraffin, isoparaffin, a rosin ester derivative such as Hercolyn, glycol ethers such as 3-methoxy-3-methyl-1-butanol, ethyl carbitol (diethylene glycol monoethyl ether), ethylene glycol monomethyl ether, propylene glycol monomethyl ether, ethylene glycol monoethyl ether, dipropylene glycol monomethyl ether, tripropylene glycol methyl ether, dipropylene glycol dimethyl ether, dipropylene glycol propyl ether, dipropylene glycol methyl ether acetate and dipropylene glycol butyl ether, a terpene resin such as pinene polymer, silicones such as cyclic silicone, and water, or a fixative.

Furthermore, the fragrance composition of the present invention may further contain, if desired, known components such as higher alcohol, surfactant, antioxidant, ultraviolet absorber, chelating agent, solubilizing agent, stabilizing agent, cooling sensation agent, preservative, antimicrobial, bactericide, fungicide, insecticidal component and coloring matter.

The production method of the fragrance composition of the present invention is not limited to particular one, but the fragrance composition of the present invention is obtained, for example, by mixing the above-described components in a usual manner.

The blending amount of the compound of the present invention in the fragrance composition of the present invention is not strictly limited and can be variously changed according to use of the fragrance composition but is preferably from 0.1 to 95.0 mass %, more preferably from 0.5 to 80.0 mass %.

[Aroma Product, Laundry Care Product, Hair Care Product, Cosmetic, or Cleaner]

The compound of the present invention or the fragrance composition of the present invention can be used, individually or in combination of two or more kinds, for a product such as aroma product, laundry care product, hair care product, cosmetic or cleaner.

Furthermore, in the product such as aroma product, laundry care product, hair care product, cosmetic or cleaner, for the purpose of letting the scent emitted from the product itself, the scent during use of the product, and the lingering scent from clothing, hair or skin be more favorable, in addition to the compound of the present invention or the fragrance composition of the present invention, there may be appropriately blended in combination a compounded fragrance; a powder fragrance or scent capsule of a known core-shell type, a matrix type using starch or processed starch, etc.; a scent-impregnated material prepared by impregnating an inorganic porous material such as silica gel or calcium silicate or an organic porous material such as celluloses, with a fragrance; a scent inclusion complex prepared by including a fragrance in α-cyclodextrin, β-cyclodextrin, γ-cyclodextrin, hydroxypropylated β-cyclodextrin, highly branched cyclic dextrin, etc.; a known fragrance precursor such as silicic acid ester compound, fatty acid ester compound, acetal compound, hemiacetal compound, Schiff base compound, hemiaminal compound or hydrazone compound, each of which can release a fragrance component; a pro-fragrance; a scent precursor; a pro-perfume, etc.

The aroma product includes, for example, a perfume, eau de cologne, a liquid air freshener, a gel air freshener, a powder air freshener, an impregnated air freshener, a mist air freshener, an aerosol air freshener, a thermal evaporation air freshener, an incense stick, a candle, etc.

The laundry care product include, for example, a mist for clothing, a spray for clothing, a laundry detergent, a fabric softener, etc.

The hair care product includes, for example, a hair shampoo, a hair rinse, a hair conditioner, a hair treatment, a hair tonic, a hair styling agent, a hair dye, a permanent waving agent, a hair growth agent, a hair cologne, etc.

The cosmetic includes, for example, a lotion, a milky lotion, a cosmetic cream, a soap, a liquid soap, a facial cleanser, a sunscreen, an antiperspirant, a bath additive, a lipstick, a foundation, etc.

The cleaner includes, for example, a toilet cleaner, a toilet bowl cleaner, a glass cleaner, a kitchen detergent, a washing machine cleaner, a drain cleaner, a bathroom cleaner, etc.

The compound of the present invention releases a fragrance component by the action of a hydrolase and therefore, is particularly useful when a product having blended therein the compound of the present invention is used in combination with a product having blended therein a hydrolase.

The method for using the products in combination is not limited to particular one but includes a method of using a mutual combination of laundry care products, hair care products, or cosmetics.

The mutual combination of laundry care products includes, for example, (A) a method in which a laundry detergent having blended therein a lipase is used in combination with a mist for clothing, a spray for clothing, a fabric softener, etc. having blended therein the compound of the present invention, and (B) a method in which a laundry detergent having blended therein the compound of the present invention is used in combination with a mist for clothing, a spray for clothing, a fabric softener, etc. having blended therein a lipase.

The mutual combination of hair care products includes, for example, (A) a method in which a shampoo having blended therein a lipase is used in combination with a hair rinse, a hair conditioner, a hair treatment, a hair styling agent, a hair growth agent, a hair cologne, etc. having blended therein the compound of the present invention, and (B) a method in which a shampoo having blended therein the compound of the present invention is used in combination with a hair rinse, a hair conditioner, a hair treatment, a hair styling agent, a hair growth agent, a hair cologne, etc., having blended therein a lipase.

The blending amount of the compound of the present invention in each product is not strictly limited and can be variously changed according to use thereof but is preferably from 0.0001 to 10 mass %, more preferably from 0.001 to 5 mass %.

[Deodorant]

The compound of the present invention or the fragrance composition of the present invention can be used, individually or in combination of two or more kinds, for a deodorant.

The deodorant of the present invention can be used after making a formulating by optionally blending one kind or two or more kinds of known components selected from a cleaner, an antimicrobial, a fungicide, a deodorant, a natural essential oil, a fragrance, an aroma material, a cooling sensation agent, a warming sensation agent, a rust inhibitor, an antifoaming agent, a pH adjusting agent, water, a solvent, a propellant, a surfactant, an insecticide, a repellent, an insect repellent, a water repellent, a degrading enzyme, an antistatic agent, a coloring matter, an ultraviolet absorber, a preservative, a chelating agent, an antioxidant, a thickener, a gellant, a water-absorbing resin, activated carbon, silica, a porous material, a resin, paper, felt, a higher alcohol, an inorganic salt, etc.

Examples thereof include a cleaner such as alkylamine oxide, alkylamine, alkyl polyglycoside, naphthalenesulfonic acid-formalin condensate, hydrolyzed collagen peptide salt, acylmethyltaurine salt, N-acylamino acid salt, alkyl sulfate, ether carboxylate, ether sulfonate, alkyltrimethylammonium chloride, dialkyltrimethylammonium chloride, alkylamine salt, alkylamidopropyl amino oxide, alkyl betaine, acetic acid betaine, fatty acid soap, etc.; an antimicrobial such as 4-chloro-3,5-xylenol, isopropylmethylphenol, thymol, hinokitiol, phenol-based compound, polyphenol, catechin, tannin, natural products containing these, natural product containing their derivatives, etc., 2-(4'-thiazolyl)-benzimidazole, benzalkonium chloride, benzethonium chloride, cetylpyridinium chloride, triclosan, silver ion, stabilized chlorine dioxide, etc.; a fungicide; a deodorant such as lauryl methacrylate, geranyl crotonate, myristic acid acetophenone, glyoxal, abietic acid, flavonoid, polyphenol, plant extract, amphoteric surfactant, zinc ricinoleate, etc.; a natural essential oil such as lemon oil, orange oil, lime oil, bergamot oil, lavandin oil, lavender oil, geranium oil, rose oil, sandalwood oil, etc.; hydrocarbons such as $\alpha$-pinene, $\beta$-pinene, limonene, p-cymene, thujone, etc.; aliphatic alcohols such as octanol, p-tert-butylcyclohexanol, etc.; terpene-based alcohols such as menthol, citronellol, geraniol, etc.; aromatic alcohols such as benzyl alcohol, phenylethyl alcohol, etc.; a fragrance, for example, aliphatic aldehydes, terpene-based aldehydes, aromatic aldehydes, acetals, chain ketones, cyclic ketones such as damascone, $\beta$-ionone, methylionone, etc., terpene-based ketones such as carvone, menthone, isomenthone, camphor, etc., aromatic ketones such as acetophenone, raspberry ketone, etc., ethers such as dibenzyl ether, etc., oxides such as linalool oxide, rose oxide, etc., musks such as cyclopentadecanolide, cyclohexadecanolide, etc., lactones such as $\gamma$-nonalactone, $\gamma$-undecalactone, coumarin, etc., aliphatic esters such as acetic acid ester, propionic acid ester, etc., and aromatic esters such as benzoic acid ester, phenylacetic acid ester, etc.; a compounded fragrance prepared from the above-described natural essential oil and fragrance; a powder fragrance or scent capsule of a known core-shell type, a matrix type using starch or processed starch, etc.; a scent-impregnated material prepared by impregnating an inorganic porous material such as silica gel, calcium silicate, etc., or an organic porous material such as celluloses, etc., with a fragrance; a scent inclusion complex prepared by including a fragrance in $\alpha$-cyclodextrin, $\beta$-cyclodextrin, $\gamma$-cyclodextrin, hydroxypropylated $\beta$-cyclodextrin, highly branched cyclic dextrin, etc.; an aroma material, for example, a known fragrance precursor, pro-fragrance, scent precursor, pro-perfume, etc., such as silicic acid ester compound, fatty acid ester compound, acetal compound, hemiacetal compound, Schiff base compound, hemiaminal compound, hydrazone compound, etc., which can release a fragrance component; a rust inhibitor such as trisodium citrate, ammonium citrate, sodium nitrite, ammonium benzoate, ammonium nitrite, etc.; an antifoaming agent such as silicone, etc.; a pH adjusting agent such as citric acid, sodium monohydrogenphosphate, sodium dihydrogenphosphate, potassium monohydrogenphosphate, potassium dihydrogenphosphate, etc.; a solvent, for example, water, ethyl alcohol, propyl alcohol, isopropyl alcohol, butyl alcohol, modified alcohol, ethylene glycol, propylene glycol, dipropylene glycol, butylene glycol, pentylene glycol, hexylene glycol, polyethylene glycol, diethyl phthalate, isopropyl myristate, triethyl citrate, benzyl benzoate, glycerin, triacetin, benzyl alcohol, paraffin, isoparaffin, a rosin ester derivative such as Hercolyn, etc., glycol ethers such as 3-methoxy-3-methyl-1-butanol, ethyl carbitol (diethylene glycol monoethyl ether), ethylene glycol monomethyl ether, propylene glycol monomethyl ether, ethylene glycol monoethyl ether, dipropylene glycol monomethyl ether, tripropylene glycol methyl ether, dipropylene glycol dimethyl ether, dipropylene glycol propyl ether, dipropylene glycol methyl ether acetate, dipropylene glycol butyl ether, etc., a terpene resin such as pinene polymer, etc., and silicones such as cyclic silicone, etc.; a propellant, for example, a liquefied petroleum gas such as propane, n-butane, isobutane, etc., a liquefied gas such as dimethyl ether, fluorocarbon (e.g., CFC (Chloro Fluoro Carbon), HCFC (Hydro Chloro Fluoro Carbon), HFC (Hydro Fluoro Carbon)), etc., and a compressed gas such as nitrogen, carbon dioxide, compressed air, nitrous oxide, etc.; and a surfactant such as polyoxyethylene alkyl ether, polyoxyethylene-polyoxypropylene copolymer, polyoxyethylene hydrogenated castor oil, sorbitan fatty acid ester, etc.

The formulated deodorant of the present invention includes, for example, a deodorizing mist, a deodorizing spray, a liquid deodorant, a gel deodorant, a solid deodorant, a cream deodorant, a sheet-shaped deodorant, a granular deodorant, a beads deodorant, a powder deodorant, a smoke deodorant, a deodorant for toilet odor, a deodorant for urine odor, a deodorant for body odor, a deodorant for sweat odor, a deodorant for foot odor, a deodorant for scalp odor, a deodorant for aging odor, a deodorant for nursing care, a deodorant for raw garbage odor, a fabric deodorizer, a deodorant for damp-dry odor, a deodorant for laundry care, a deodorant for shoe cupboards, a shoe deodorizer, an entrance deodorizer, a room deodorizer, a bedroom deodorizer, a car freshener, a deodorant for drain odor, a deodorant for pets, a deodorant for diapers, a deodorant for closets, a deodorant for air conditioners, etc.

The deodorant of the present invention can be used in a product such as aroma product, laundry care product, hair care product, cosmetic, oral care product, hygiene product, insecticide, insect repellent, dehumidifying agent, cleaner, etc.

The aroma product includes, for example, a liquid air freshener, a gel air freshener, a powder air freshener, an impregnated air freshener, a beads air freshener, a paper air freshener, a permeable film air fresher, a plug-type air freshener, a fan-type air freshener, an ultrasonic air freshener, a water-absorbing polymer air freshener, a mist air freshener, an aerosol air freshener, a thermal evaporation air freshener, an incense stick, a candle, a reed diffuser, etc., to which a deodorizing function is imparted.

The laundry care product includes, for example, a mist for clothing, a spray for clothing, a laundry detergent, a fabric softener, an anti-wrinkle agent, etc., to which a deodorizing function is imparted.

The hair care product includes, for example, a hair shampoo, a hair rinse, a hair conditioner, a hair treatment, a hair tonic, a hair styling agent, a hair dye, a permanent waving agent, a hair growth agent, a hair lotion, a hair spray, etc., to which a deodorizing function is imparted.

The cosmetic includes, for example, a lotion, a milky lotion, a cosmetic cream, a soap, a liquid soap, a facial cleanser, a sunscreen, an antiperspirant, a bath additive, a lipstick, a foundation, etc., to which a deodorizing function is imparted.

The oral care product includes, for example, a toothpaste, a mouthwash, a mouth spray, a mouth freshener, a denture care product, a breath freshening product, etc., to which a deodorizing function is imparted.

The hygiene product includes, for example, a paper diaper, a sanitary product, wet tissue, tissue paper, toilet paper, a mask, etc., to which a deodorizing function is imparted.

The cleaner includes, for example, a toilet cleaner, a toilet bowl cleaner, a glass cleaner, a kitchen detergent, a washing machine cleaner, a drain cleaner, a bathroom cleaner, a denture cleaner, etc., to which a deodorizing function is imparted.

The blending amount of the compound of the present invention in each product is not strictly limited and can be variously changed according to use thereof. The blending amount of the compound of the present invention in each product is preferably from 0.0001 to mass %, more preferably from 0.001 to 5 mass %.

EXAMPLES

The present invention is specifically described below by referring to Examples, but the present invention is not limited thereto. Note that in Examples, unless otherwise specified, "parts" and "%" are on a mass basis.

(Example 1) Synthesis of 3,7-dimethyl-6-octenyl benzoate (citronellyl benzoate)

[Chem. 9]

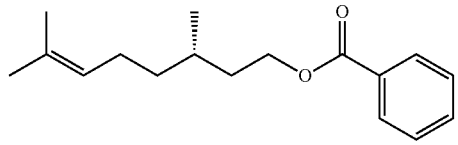

To 31.2 mL of a toluene solution containing 1.56 g (10 mmol) of (S)-citronellol, 2.79 mL (20 mmol) of triethylamine and 12.2 mg (0.1 mmol) of N,N-dimethylaminopyridine, 1.69 g (12 mmol) of benzoic acid chloride was added at 0° C., followed by stirring at room temperature for 24 hours.

After cooling the reaction solution, the reaction was quenched by the addition of water, and the solution was extracted with toluene. The organic layer was washed with water and then concentrated under reduced pressure to obtain a crude product. The resulting crude product was purified by silica gel column chromatography to obtain 2.28 g of the target product.

(Example 2) Synthesis of 1-((1R,6S)-2,2,6-trimethylcyclohexyl)-3-hexanyl Benzoate

[Chem. 10]

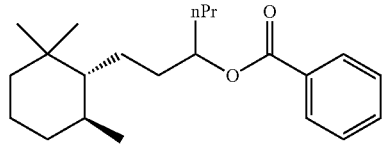

To 15.8 mL of a tetrahydrofuran solution containing 1.05 g (4.64 mmol) of 1-((1R,6S)-trimethylcyclohexyl)-3-hexanol, 3.23 mL (5.10 mmol) of n-butyllithium was added at 0° C., followed by stirring at 0° C. for 1 hour. Thereafter, 0.72 g (5.10 mmol) of benzoic acid chloride was added, and the resulting mixture was stirred at 0° C. for 1 hour and at room temperature for 5 hours.

After cooling the reaction solution, the reaction was quenched by the addition of an aqueous ammonium chloride solution, and the solution was extracted with toluene. The organic layer was washed with water and then concentrated under reduced pressure to obtain a crude product. The resulting crude product was purified by silica gel column chromatography to obtain 1.50 g of the target product.

(Example 3) Synthesis of 1-((R,6S)-2,2,6-trimethyl-cyclohexyl)-3-hexanyl Anisate

[Chem. 11]

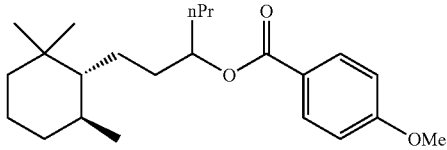

To 15.8 mL of a tetrahydrofuran solution containing 1.05 g (4.64 mmol) of 1-((1R,6S)-trimethylcyclohexyl)-3-hexanol, 3.23 mL (5.10 mmol) of n-butyllithium was added at 0° C., followed by stirring at 0° C. for 1 hour. Thereafter, 0.87 g (5.10 mmol) of p-methoxybenzoic acid chloride was added, and the resulting mixture was stirred at 0° C. for 1 hour and at room temperature for 5 hours.

After cooling the reaction solution, the reaction was quenched by the addition of an aqueous ammonium chloride solution, and the solution was extracted with toluene. The organic layer was washed with water and then concentrated under reduced pressure to obtain a crude product. The resulting crude product was purified by silica gel column chromatography to obtain 1.60 g of the target product.

(Example 4) Synthesis of 1-((1R,6S)-2,2,6-trimethylcyclohexyl)-3-hexanyl Toluate

[Chem. 12]

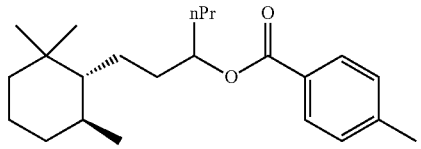

To 15.8 mL of a tetrahydrofuran solution containing 1.05 g (4.64 mmol) of 1-((1R,6S)-trimethylcyclohexyl)-3-hexanol, 3.23 mL (5.10 mmol) of n-butyllithium was added at 0° C., followed by stirring at 0° C. for 1 hour. Thereafter, 0.79 g (5.10 mmol) of p-methylbenzoic acid chloride was added, and the resulting mixture was stirred at 0° C. for 0.5 hours and at room temperature for 2 hours.

After cooling the reaction solution, the reaction was quenched by the addition of an aqueous ammonium chloride solution, and the solution was extracted with toluene. The organic layer was washed with water and then concentrated under reduced pressure to obtain a crude product. The resulting crude product was purified by silica gel column chromatography to obtain 1.50 g of the target product.

(Example 5) Synthesis of 1-((R,6S)-2,2,6-trimethyl-cyclohexyl)-3-hexanyl Cinnamate

[Chem. 13]

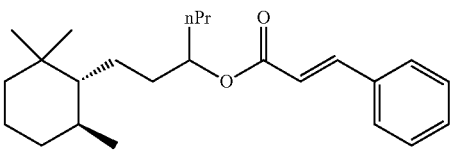

To 15.8 mL of a tetrahydrofuran solution containing 1.05 g (4.64 mmol) of 1-((1R,6S)-trimethylcyclohexyl)-3-hexanol, 3.23 mL (5.10 mmol) of n-butyllithium was added at 0° C., followed by stirring at 0° C. for 1 hour. Thereafter, 0.85 g (5.10 mmol) of cinnamoyl chloride was added, and the resulting mixture was stirred at 0° C. for 1 hour and at room temperature for 5 hours.

After cooling the reaction solution, the reaction was quenched by the addition of an aqueous ammonium chloride solution, and the solution was extracted with toluene. The organic layer was washed with water and then concentrated under reduced pressure to obtain a crude product. The resulting crude product was purified by silica gel column chromatography to obtain 1.57 g of the target product.

(Example 6) Synthesis of (1R,2S,5R)-isopropyl-5-methylcyclohexyl benzoate (menthyl benzoate)

[Chem. 14]

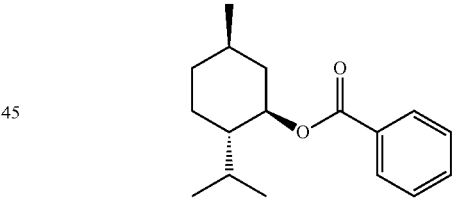

To 23.4 mL of a tetrahydrofuran solution containing 1.56 g (10 mmol) of (1R,2S,5R)-2-isopropyl-5-methylcyclohexanol, 6.65 mL (10.5 mmol) of n-butyllithium was added at 0° C., followed by stirring at 0° C. for 1 hour. Thereafter, 1.48 g (10.5 mmol) of benzoic acid chloride was added, and the resulting mixture was stirred at 0° C. for 1.0 hours and at room temperature for 4 hours.

After cooling the reaction solution, the reaction was quenched by the addition of an aqueous ammonium chloride solution, and the solution was extracted with toluene. The organic layer was washed with water and then concentrated under reduced pressure to obtain a crude product. The resulting crude product was purified by silica gel column chromatography to obtain 2.55 g of the target product.

(Example 7) Synthesis of
(S,E)-3,7,11-trimethyl-6,10-dodecadienyl Benzoate

[Chem. 15]

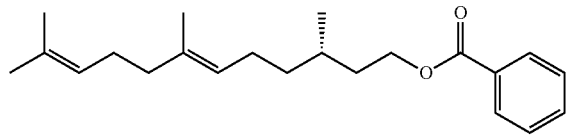

To 22.4 mL of a toluene solution containing 1.12 g (5 mmol) of (S)-dihydrofarnesol, 1.39 mL (10 mmol) of triethylamine and 12.2 mg (0.1 mmol) of N,N-dimethylaminopyridine, 0.84 g (6 mmol) of benzoic acid chloride was added at 0° C., followed by stirring at room temperature for 24 hours.

After cooling the reaction solution, the reaction was quenched by the addition of water, and the solution was extracted with toluene. The organic layer was washed with water and then concentrated under reduced pressure to obtain a crude product. The resulting crude product was purified by silica gel column chromatography to obtain 1.58 g of the target product.

(Example 8) Synthesis of
(S,E)-3,7,11-trimethyl-6,10-dodecadienyl Anisate

[Chem. 16]

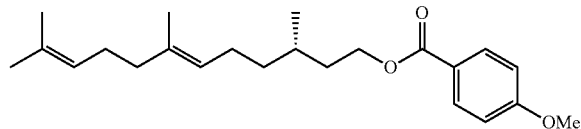

To 22.4 mL of a toluene solution containing 1.12 g (5 mmol) of (S)-dihydrofarnesol, 1.39 mL (10 mmol) of triethylamine and 12.2 mg (0.1 mmol) of N,N-dimethylaminopyridine, 1.02 g (6 mmol) of p-methoxybenzoic acid chloride was added at 0° C., followed by stirring at room temperature for 24 hours.

After cooling the reaction solution, the reaction was quenched by the addition of water, and the solution was extracted with toluene. The organic layer was washed with water and then concentrated under reduced pressure to obtain a crude product. The resulting crude product was purified by silica gel column chromatography to obtain 1.58 g of the target product.

(Example 9) Synthesis of
(S,E)-3,7,11-trimethyl-6,10-dodecadienyl Toluate

[Chem. 17]

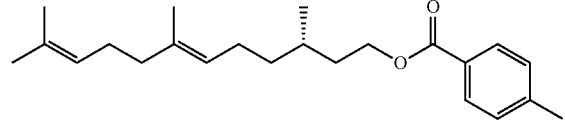

To 22.4 mL of a toluene solution containing 1.12 g (5 mmol) of (S)-dihydrofarnesol, 1.39 mL (10 mmol) of triethylamine and 12.2 mg (0.1 mmol) of N,N-dimethylaminopyridine, 0.93 g (6 mmol) of p-methylbenzoic acid chloride was added at 0° C., followed by stirring at room temperature for 24 hours.

After cooling the reaction solution, the reaction was quenched by the addition of water, and the solution was extracted with toluene. The organic layer was washed with water and then concentrated under reduced pressure to obtain a crude product. The resulting crude product was purified by silica gel column chromatography to obtain 1.59 g of the target product.

(Example 10) Synthesis of
(S,E)-3,7,11-trimethyl-6,10-dodecadienyl Cinnamate

[Chem. 18]

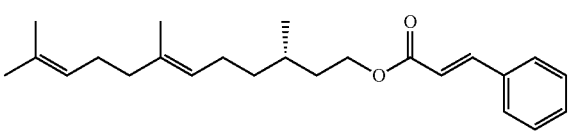

To 22.4 mL of a toluene solution containing 1.12 g (5 mmol) of (S)-dihydrofarnesol, 1.39 mL (10 mmol) of triethylamine and 12.2 mg (0.1 mmol) of N,N-dimethylaminopyridine, 1.20 g (7.2 mmol) of cinnamoyl chloride was added at 0° C., followed by stirring at room temperature for 24 hours.

After cooling the reaction solution, the reaction was quenched by the addition of water, and the solution was extracted with toluene. The organic layer was washed with water and then concentrated under reduced pressure to obtain a crude product. The resulting crude product was purified by silica gel column chromatography to obtain 1.55 g of the target product.

(Example 11) Synthesis of (Z)-3-hexenyl Benzoate

[Chem. 19]

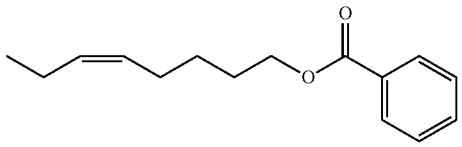

To 30 mL of a toluene solution containing 1.00 g (10 mmol) of (Z)-3-hexenol, 2.79 mL (20 mmol) of triethylamine and 12.2 mg (0.1 mmol) of N,N-dimethylaminopyridine, 1.69 g (12 mmol) of benzoic acid chloride was added at 0° C., followed by stirring at room temperature for 24 hours.

After cooling the reaction solution, the reaction was quenched by the addition of water, and the solution was extracted with toluene. The organic layer was washed with water and then concentrated under reduced pressure to obtain a crude product. The resulting crude product was purified by silica gel column chromatography to obtain 1.90 g of the target product.

(Example 12) Synthesis of 4-allyl-2-methoxyphenyl benzoate

[Chem. 20]

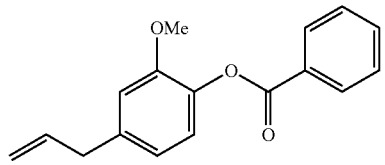

To 41.0 mL of a toluene solution containing 1.64 g (10 mmol) of eugenol, 2.09 mL (15 mmol) of triethylamine and 12.2 mg (0.1 mmol) of N,N-dimethylaminopyridine, 1.69 g (12 mmol) of benzoic acid chloride was added at 0° C., followed by stirring at room temperature for 24 hours.

After cooling the reaction solution, the reaction was quenched by the addition of water, and the solution was extracted with toluene. The organic layer was washed with water and then concentrated under reduced pressure to obtain a crude product. The resulting crude product was purified by silica gel column chromatography to obtain 2.67 g of the target product.

(Example 13) Synthesis of 4-formyl-2-methoxyphenyl Benzoate

[Chem. 21]

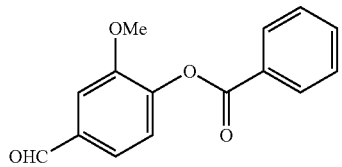

To 38.0 mL of a toluene solution containing 1.52 g (10 mmol) of vanillin, 2.09 mL (15 mmol) of triethylamine and 12.2 mg (0.1 mmol) of N,N-dimethylaminopyridine, 1.69 g (12 mmol) of benzoic acid chloride was added at 0° C., followed by stirring at room temperature for 24 hours.

After cooling the reaction solution, the reaction was quenched by the addition of water, and the solution was extracted with toluene. The organic layer was washed with water and then concentrated under reduced pressure to obtain a crude product. The resulting crude product was purified by silica gel column chromatography to obtain 2.54 g of the target product.

(Example 14) Synthesis of 9-decenyl Benzoate

[Chem. 22]

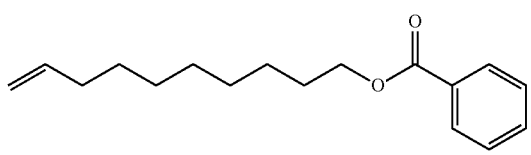

To 31.2 mL of a toluene solution containing 1.56 g (10 mmol) of 9-decen-1-ol, 2.79 mL (20 mmol) of triethylamine and 12.2 mg (0.1 mmol) of N,N-dimethylaminopyridine, 1.69 g (12 mmol) of benzoic acid chloride was added at 0° C., followed by stirring at room temperature for 5 hours.

After cooling the reaction solution, the reaction was quenched by the addition of water, and the solution was extracted with toluene. The organic layer was washed with water and then concentrated under reduced pressure to obtain a crude product. The resulting crude product was purified by silica gel column chromatography to obtain 2.54 g of the target product.

(Examples 15 to 33) Lipase-Induced Scent Emission Test 10 mg of a fragrance precursor and 1 g of an aqueous 1% lipase preparation solution were put in a vial bottle and mixed and after hermetically sealing the bottle, the mixture was subjected to GC/MS analysis of the head space component to obtain a peak area of the scent-emitting compound. As a control, water was used in place of the aqueous 1% lipase preparation solution, and a peak area of the control was obtained by the same method. The scent emission amount was determined from the difference between the obtained peak area of the scent-emitting compound and the peak area of the control. The results are shown in Tables 13 and 14.

(GC/MS Measurement Conditions)
Measurement instrument: 7890GC/5975M (manufactured by Agilent Technologies)
Column: BC-WAX50 m×0.25 mm I.D.
Temperature rise: 70° C. to 220° C., 4° C./min
Split ratio: 60:1

TABLE 13

Scent emission by the action of lipase preparation AY "Amano" 30SD (produced by Amano Enzyme Inc.)

| Example | Fragrance Precursor | Scent Emission Amount | Scent-Emitting Compound |
|---|---|---|---|
| 15 | compound of Example 11 | 49,663,459 | (Z)-3-hexenol |
| 16 | (Z)-3-hexenyl salicylate | 16,933,990 | (Z)-3-hexenol |
| 17 | geranyl benzoate | 78,461,812 | geraniol |
| 18 | phenylethyl benzoate | 96,460,830 | phenylethyl alcohol |
| 19 | compound of Example 6 | 82,023,336 | menthol |
| 20 | phenylethyl phenylacetate | 50,855,859 | phenylethyl alcohol |
| 21 | geranyl phenylacetate | 54,842,763 | geraniol |
| 22 | rosinyl phenylacetate | 56,492,946 | rosinol |
| 23 | cinnamyl cinnamate | 24,711,289 | cinnamic alcohol |
| 24 | phenylethyl cinnamate | 22,892,002 | phenylethyl alcohol |
| 25 | compound of Example 7 | 88,986,381 | dihydrofarnesol |
| 26 | compound of Example 8 | 23,338,647 | dihydrofarnesol |
| 27 | compound of Example 9 | 19,259,897 | dihydrofarnesol |
| 28 | compound of Example 3 | 40,373,157 | 1-((1R,6S)-trimethylcyclohexyl)-3-hexanol |

TABLE 14

Scent emission by the action of lipase preparation Lipex 100 L (produced by Novozymes)

| Example | Fragrance Precursor | Scent Emission Amount | Scent-Emitting Compound |
|---|---|---|---|
| 29 | compound of Example 1 | 28,098,876 | citronellol |
| 30 | compound of Example 12 | 164,744,420 | eugenol |

TABLE 14-continued

Scent emission by the action of lipase preparation Lipex 100 L (produced by Novozymes)

| Example | Fragrance Precursor | Scent Emission Amount | Scent-Emitting Compound |
|---|---|---|---|
| 31 | compound of Example 13 | 47,188,750 | vanillin |
| 32 | compound of Example 10 | 19,967,420 | dihydrofarnesol |
| 33 | compound of Example 3 | 40,430,750 | 1-((1R,6S)-trimethylcyclohexyl)-3-hexanol |

(Examples 34 and 35, Comparative Example 1) Test for Confirming Scent Emission from Hair when Using Shampoo Shampoos were prepared according to the formulation shown in Table 15. A hair bundle of 10 cm in length was cleaned using the prepared shampoo and rinsed with tap water. After drying at room temperature for 15 hours, about 0.3 g of an aqueous 1%/lipase preparation solution was sprayed onto the hair bundle, and the scent on the hair bundle was smelled to examine the presence or absence of scent emission from hair. As the lipase preparation, AY "Amano" 30SD was used.

TABLE 15

Formulation of shampoo (mass %)

| Raw Material | Example 34 | Example 35 | Comparative Example 1 |
|---|---|---|---|
| Sodium polyoxyethylene lauryl ether sulfate | 14 | 14 | 14 |
| Laurylsulfuric acid amidopropyl betaine | 4 | 4 | 4 |
| Coconut fatty acid diethanolamide | 3 | 3 | 3 |
| Cationized cellulose | 0.5 | 0.5 | 0.5 |
| Ethylene glycol distearate | 1 | 1 | 1 |
| Paraoxybenzoic acid ester | 0.2 | 0.2 | 0.2 |
| Geranyl benzoate | 0.3 | 0 | 0 |
| Compound of Example 12 | 0 | 0.3 | 0 |
| Geraniol | 0 | 0 | 0.3 |
| Deionized water | 77 | 77 | 77 |
| Total (mass %) | 100 | 100 | 100 |

It could be confirmed that the geraniol odor is emitted by reacting the hair after drying obtained using the shampoo prepared in Example 34 with lipase.

It could be confirmed that the eugenol odor is emitted by reacting the hair after drying obtained using the shampoo prepared in Example 35 with lipase.

The hair after drying obtained using the shampoo prepared in Comparative Example 1 was reacted with lipase, but an odor could not be confirmed.

(Examples 36 and 37, Comparative Example 2) Test for Confirming Scent Emission from Hair when Using Hair Conditioner Hair conditioners were prepared according to the formulation shown in Table 16. A hair bundle of 10 cm in length was treated with the hair conditioner prepared and rinsed with tap water. After drying at room temperature for 15 hours, about 0.3 g of an aqueous 1% lipase preparation solution was sprayed onto the hair bundle, and the odor on the hair bundle was smelled to examine the presence or absence of scent emission from hair. As the lipase preparation, AY "Amano" 30SD was used.

TABLE 16

Formulation of hair conditioner (mass %)

| Raw Material | Example 36 | Example 37 | Comparative Example 2 |
|---|---|---|---|
| Stearyltrimethylammonium chloride | 0.5 | 0.5 | 0.5 |
| Distearyldimethylammonium chloride | 1.5 | 1.5 | 1.5 |
| Cetanol | 4.5 | 4.5 | 4.5 |
| Amino-modified silicone | 0.5 | 0.5 | 0.5 |
| Glycerin | 5 | 5 | 5 |
| Paraoxybenzoic acid ester | 0.2 | 0.2 | 0.2 |
| Compound of Example 6 | 0.3 | 0 | 0 |
| Compound of Example 1 | 0 | 0.3 | 0 |
| Citronellol | 0 | 0 | 0.3 |
| Deionized water | 87.5 | 87.5 | 87.5 |
| Total (mass %) | 100 | 100 | 100 |

It could be confirmed that the menthol odor is emitted by reacting the hair after drying obtained using the hair conditioner prepared in Example 36 with lipase.

It could be confirmed that the citronellol odor is emitted by reacting the hair after drying obtained using the hair conditioner prepared in Example 37 with lipase.

The hair after drying obtained using the hair conditioner prepared in Comparative Example 2 was reacted with lipase, but an odor could not be confirmed.

(Examples 38 to 40, Comparative Example 3) Test for Confirming Scent Emission from Towel when Using Liquid Detergent Liquid detergents were prepared according to the formulation shown in Table 17. A cotton towel was cleaned with the liquid detergent prepared and rinsed with tap water. After drying at room temperature for 15 hours, about 0.3 g of an aqueous 1% lipase preparation solution was sprayed onto the towel, and the odor on the towel was smelled to examine the presence or absence of scent emission from towel. As the lipase preparation, AY "Amano" 30SD was used.

TABLE 17

Formulation of liquid detergent (mass %)

| Raw Material | Example 38 | Example 39 | Example 40 | Comparative Example 3 |
|---|---|---|---|---|
| Polyoxyethylene alkyl ether | 40 | 40 | 40 | 40 |
| Linear alkylbenzenesulfonate | 18 | 18 | 18 | 18 |
| Butyl carbitol | 10 | 10 | 10 | 10 |
| Propylene glycol | 3 | 3 | 3 | 3 |
| Monoethanolamine | 3 | 3 | 3 | 3 |
| Phenylethyl salicylate | 0.5 | 0 | 0 | 0 |
| Compound of Example 1 | 0 | 0.5 | 0 | 0 |
| Compound of Example 12 | 0 | 0 | 0.5 | 0 |
| Phenylethyl alcohol | 0 | 0 | 0 | 0.5 |
| Deionized water | 25.5 | 25.5 | 25.5 | 25.5 |
| Total (mass %) | 100 | 100 | 100 | 100 |

It could be confirmed that the phenylethyl alcohol odor is emitted by reacting the towel after drying obtained using the liquid detergent prepared in Example 38 with lipase.

It could be confirmed that the citronellol odor is emitted by reacting the towel after drying obtained using the liquid detergent prepared in Example 39 with lipase.

It could be confirmed that the eugenol odor is emitted by reacting the towel after drying obtained using the liquid detergent prepared in Example 40 with lipase.

The towel after drying obtained using the liquid detergent prepared in Comparative Example 3 was reacted with lipase, but an odor could not be confirmed.

(Examples 41 to 43, Comparative Example 4) Test for Confirming Scent Emission from Towel when Using Softener Softeners were prepared according to the formulation shown in Table 18. A cotton towel was treated with the softener prepared and rinsed with tap water. After drying at room temperature for 15 hours, about 0.3 g of an aqueous 1% lipase preparation solution was sprayed onto the towel, and the odor on the towel was smelled to examine the presence or absence of scent emission from towel. As the lipase preparation, AY "Amano" 30SD was used.

TABLE 18

Formulation of softener (mass %)

| Raw Material | Example 41 | Example 42 | Example 43 | Comparative Example 4 |
|---|---|---|---|---|
| Tri(oxyethylene)methyl-ammonium methylsulfate fatty acid ester | 18 | 18 | 18 | 18 |
| Polyoxyethylene(23) lauryl ether | 3 | 3 | 3 | 3 |
| Propylene glycol | 3 | 3 | 3 | 3 |
| Calcium chloride | 0.1 | 0.1 | 0.1 | 0.1 |
| Phenylethyl benzoate | 0.5 | 0 | 0 | 0 |
| Geranyl phenylacetate | 0 | 0.5 | 0 | 0 |
| Compound of Example 7 | 0 | 0 | 0.5 | 0 |
| Geraniol | 0 | 0 | 0 | 0.5 |
| Deionized water | 75.4 | 75.4 | 75.4 | 75.4 |
| Total (mass %) | 100 | 100 | 100 | 100 |

It could be confirmed that the phenylethyl alcohol odor is emitted by reacting the towel after drying obtained using the softener prepared in Example 41 with lipase.

It could be confirmed that the geraniol odor is emitted by reacting the towel after drying obtained using the softener prepared in Example 42 with lipase.

It could be confirmed that the dihydrofarnesol odor is emitted by reacting the towel after drying obtained using the softener prepared in Example 43 with lipase.

The towel after drying obtained using the softener prepared in Comparative Example 4 was reacted with lipase, but an odor could not be confirmed.

(Examples 44 and 45, Comparative Example 5) Fragrance Composition

Fragrance compositions were prepared according to the formulation shown in Table 19.

TABLE 19

Formulation of fragrance composition (parts by mass)

| Raw Material | Example 44 | Example 45 | Comparative Example 5 |
|---|---|---|---|
| Undecylene aldehyde | 5 | 5 | 5 |
| Allylamyl glycolate | 2 | 2 | 2 |
| Allyl enanthate | 5 | 5 | 5 |
| Benzyl acetate | 10 | 10 | 10 |
| Borneol | 5 | 5 | 5 |
| Cinnamic alcohol | 8 | 8 | 8 |
| Citronellol | 50 | 50 | 50 |

TABLE 19-continued

Formulation of fragrance composition (parts by mass)

| Raw Material | Example 44 | Example 45 | Comparative Example 5 |
|---|---|---|---|
| Coumarin | 3 | 3 | 3 |
| Tricyclodecenyl acetate | 60 | 60 | 60 |
| α-Damascone | 1 | 1 | 1 |
| Dihydromyrcenol | 60 | 60 | 60 |
| Diphenyl oxide | 3 | 3 | 3 |
| Eucalyptus oil | 1 | 1 | 1 |
| Geraniol | 30 | 30 | 30 |
| Methyl dihydrojasmonate | 40 | 40 | 40 |
| Hexyl cinnamic aldehyde | 40 | 40 | 40 |
| Lime oil | 25 | 25 | 25 |
| Lemon oil | 30 | 30 | 30 |
| Linalol | 80 | 80 | 80 |
| Linalyl acetate | 40 | 40 | 40 |
| MUSK T (produced by Takasago International Corporation) | 100 | 100 | 100 |
| γ-Methylionone | 20 | 20 | 20 |
| Methyl nonyl ketone | 2 | 2 | 2 |
| Nerol | 20 | 20 | 20 |
| ORBITONE (produced by Takasago International Corporation) | 40 | 40 | 40 |
| 4-tert-Butylcyclohexanol | 20 | 20 | 20 |
| p-tert-Butylcyclohexyl acetate | 100 | 100 | 100 |
| Geranyl phenylacetate | 200 | 0 | 0 |
| Compound of Example 3 | 0 | 200 | 0 |
| Dipropylene glycol | 0 | 0 | 200 |
| Total (parts by mass) | 1000 | 1000 | 1000 |

MUSK T (registered trademark)
ORBITONE (registered trademark)

(Examples 46 to 51, Comparative Examples 6 to 12) Liquid Detergent/Softener Combination Use Test Liquid detergents with or without lipase were prepared according to the formulation shown in Table 20. In addition, softeners were prepared according to the formulation shown in Table 21.

TABLE 20

Formulation of liquid detergent (mass %)

| Raw Material | With Lipase | Without Lipase |
|---|---|---|
| Polyoxyethylene alkyl ether | 40 | 40 |
| Linear alkylbenzenesulfonate | 18 | 18 |
| Butyl carbitol | 10 | 10 |
| Propylene glycol | 3 | 3 |
| Monoethanolamine | 3 | 3 |
| Lipase preparation/Lipex 100 L | 1 | — |
| Deionized water | 25 | 26 |
| Total (mass %) | 100 | 100 |

Lipex 100 L: produced by Novozymes

TABLE 21

Formulation of softener (mass %)

| Raw Material | Example 46 | Example 47 | Comparative Example 6 |
|---|---|---|---|
| Fragrance composition of Example 44 | 0.5 | 0 | 0 |
| Fragrance composition of Example 45 | 0 | 0.5 | 0 |
| Fragrance composition of Comparative Example 5 | 0 | 0 | 0.5 |

TABLE 21-continued

Formulation of softener (mass %)

| Raw Material | Example 46 | Example 47 | Comparative Example 6 |
|---|---|---|---|
| Tri(oxyethylene)methylammonium methylsulfate fatty acid ester | 18 | 18 | 18 |
| Polyoxyethylene(23) lauryl ether | 3 | 3 | 3 |
| Propylene glycol | 3 | 3 | 3 |
| Calcium chloride | 0.05 | 0.05 | 0.05 |
| Citric acid | 0.01 | 0.01 | 0.01 |
| Sodium citrate | 0.1 | 0.1 | 0.1 |
| Deionized water | 75.34 | 75.34 | 75.34 |
| Total (mass %) | 100 | 100 | 100 |

A cotton towel was cleaned with the liquid detergent obtained above, and the cotton towel after cleaning was dehydrated and then treated with the softener obtained above. After dehydration, the towel was dried overnight. The scent intensity and fresh feeling of the cotton towel during drying and after drying were evaluated by ten expert panelists according to the following evaluation criteria. The evaluation score was determined by averaging the evaluation values of the ten expert panelists. The results are shown in Tables 22 and 23.

(Evaluation Criteria of Scent Intensity)
- 0: Odorless
- 1: Barely perceivable odor
- 2: Odor can be identified as what odor but is weak
- 3: Easily perceivable odor
- 4: Strong odor
- 5: Intense odor (Evaluation Criteria of Fresh Feeling)
- 0: No fresh feeling is sensed.
- 1: Fresh feeling is faintly sensed.
- 2: Fresh feeling is slightly sensed.
- 3: Fresh feeling is sensed.
- 4: Fresh feeling is fairly sensed.

TABLE 22

Results of scent intensity

| | Example 48 | Comparative Example 7 | Example 49 | Comparative Example 8 | Comparative Example 9 |
|---|---|---|---|---|---|
| Liquid detergent | with lipase | without lipase | with lipase | without lipase | with lipase |
| Softener | Example 46 | Example 46 | Example 47 | Example 47 | Comparative Example 6 |
| During drying | 3.2 | 2.6 | 3.3 | 2.5 | 2.5 |
| After drying | 2.5 | 1.2 | 2.8 | 1.2 | 1.0 |

TABLE 23

Results of fresh feeling

| | Example 50 | Comparative Example 10 | Example 51 | Comparative Example 11 | Comparative Example 12 |
|---|---|---|---|---|---|
| Liquid detergent | with lipase | without lipase | with lipase | without lipase | with lipase |
| Softener | Example 46 | Example 46 | Example 47 | Example 47 | Comparative Example 6 |
| During drying | 3.6 | 2.4 | 3.7 | 2.6 | 2.4 |
| After drying | 2.8 | 0.5 | 3.3 | 0.7 | 0.5 |

It could be confirmed from the results in Tables 22 and 23 that when a softener using a compounded fragrance having blended therein a compound represented by general formula (1) of the present invention is used in combination with a liquid detergent having blended therein lipase, scent emission occurs and the scent intensity and the fresh feeling of lingering scent are enhanced.

It could be confirmed from the results in Tables 22 and 23 that the fragrance precursor of the present invention releases a scent-emitting compound having a hydroxy group by the action of lipase.

(Examples 52 to 68) Scent Emission Test by Microorganism (Microorganism Culturing Method)

Culture of *Staphylococcus aureus* strain NBRC12732, *Corynebacterium xerosis* strain JCM1324, *Pseudomonas aeruginosa* strain NBRC13275, and *Moraxella osloensis* strain ATCC19976:

After inoculating each of bacteria in Muller-Hinton liquid medium, shaking culture was performed at 30° C. for 20 hours, and 3 mL of the resulting preculture solution was transferred to a vial bottle. 10 mg of each of the fragrance precursors was mixed therewith and after hermetical sealing, shaking culture was further performed at 30° C. for 20 hours.

Culture of *Propionibacterium acnes* Strain JCM6473:

After inoculating the bacterium in GAM bouillon liquid medium containing Hemin 0.5 ppm and Menadione 0.5 ppm, static culture was performed at 28° C. for 3 days under anaerobic conditions, and 3 mL of the resulting preculture solution was transferred to a vial bottle. 10 mg of each of the fragrance precursors was mixed therewith and after hermetical sealing, static culture was further performed at 28° C. for 3 days.

Culture of *Malassezia furfur* Strain NBRC0656:

After inoculating the bacterium in Sabouraud liquid medium containing 0.1% Tween 80, static culture was performed at 28° C. for 3 days under anaerobic conditions, and 3 mL of the resulting preculture solution was transferred to a vial bottle. 10 mg of the fragrance precursor was mixed therewith and after hermetical sealing, static culture was further performed at 28° C. for 3 days.

(Test Method)

A peak area of the scent-emitting compound was obtained by performing GC/MS analysis of the head space component included in the vial bottle containing 3 mL of a microorganism culture solution in which 10 mg of the fragrance precursor was mixed. A microorganism culture solution having not mixed therein the fragrance precursor was used as the control, and a peak area of the control was obtained by the same method. The scent emission amount was determined from the difference between the obtained peak area of the scent-emitting compound and the peak area of the control. The results are shown in Tables 24 to 29.

(GC/MS Measurement Conditions)

Measurement instrument: 7890GC/5975MSD (manufactured by Agilent Technologies)

Column: BC-WAX 50 m×0.25 mm I.D.

Temperature rise: 70° C. to 220° C., 4° C./min

Split ratio: splitless

TABLE 24

Scent emission amount when mixed with culture solution of *Staphylococcus aureus* NBRC12732

| Example | Fragrance Precursor | Scent Emission Amount | Scent-Emitting Compound |
|---|---|---|---|
| 52 | geranyl benzoate | 839,961,157 | geraniol |
| 53 | phenylethylene cinnamate | 144,750,281 | phenylethyl alcohol |
| 54 | (Z)-3-hexenyl salicylate | 14,126,965 | (Z)-3-hexenol |

It could be confirmed from the results in Table 24 that the fragrance precursor of the present invention releases a scent-emitting compound having a hydroxy group by the action of *Staphylococcus aureus* NBRC12732.

TABLE 25

Scent emission amount when mixed with culture solution of *Corynebacterium xerosis* JCM1324

| Example | Fragrance Precursor | Scent Emission Amount | Scent-Emitting Compound |
|---|---|---|---|
| 55 | geranyl phenylacetate | 39,033,900 | geraniol |

It could be confirmed from the results in Table 25 that the fragrance precursor of the present invention releases a scent-emitting compound having a hydroxy group by the action of *Corynebacterium* xerosis JCM1324.

TABLE 26

Scent emission amount when mixed with culture solution of *Pseudomonas aeruginosa* NBRC13275

| Example | Fragrance Precursor | Scent Emission Amount | Scent-Emitting Compound |
|---|---|---|---|
| 56 | geranyl benzoate | 117,161,311 | geraniol |
| 57 | phenylethyl cinnamate | 247,508,719 | phenylethyl alcohol |
| 58 | citronellyl phenylacetate | 150,385,642 | citronellol |

It could be confirmed from the results in Table 26 that the fragrance precursor of the present invention releases a scent-emitting compound having a hydroxy group by the action of *Pseudomonas aeruginosa* NBRC13275.

TABLE 27

Scent emission amount when mixed with culture solution of *Moraxella osloensis* ATCC19976

| Example | Fragrance Precursor | Scent Emission Amount | Scent-Emitting Compound |
|---|---|---|---|
| 59 | citronellyl phenylacetate | 500,940,481 | citronellol |
| 60 | compound of Example 14 | 86,274,718 | 9-decenol |

It could be confirmed from the results in Table 27 that the fragrance precursor of the present invention releases ascent-emitting compound having a hydroxy group by the action of *Moraxella osloensis* ATCC 19976.

TABLE 28

Scent emission amount when mixed with culture solution of *Propionibacterium acnes* JCM6473

| Example | Fragrance Precursor | Scent Emission Amount | Scent-Emitting Compound |
|---|---|---|---|
| 61 | geranyl benzoate | 105,061,217 | geraniol |
| 62 | phenylethyl cinnamate | 112,497,882 | phenylethyl alcohol |
| 63 | citronellyl phenylacetate | 292,401,763 | citronellol |
| 64 | compound of Example 14 | 133,440,692 | 9-decenol |

It could be confirmed from the results in Table 28 that the fragrance precursor of the present invention releases ascent-emitting compound having a hydroxy group by the action of *Propionibacterium acnes* JCM6473.

TABLE 29

Scent emission amount when mixed with culture solution of *Malassezia furfur* NBRC0656

| Example | Fragrance Precursor | Scent Emission Amount | Scent-Emitting Compound |
|---|---|---|---|
| 65 | geranyl benzoate | 121,633,184 | geraniol |
| 66 | phenylethyl cinnamate | 351,450,490 | phenylethyl alcohol |
| 67 | citronellyl phenylacetate | 369,118,269 | citronellol |
| 68 | compound of Example 14 | 304,030,021 | 9-decenol |

It could be confirmed from the results in Table 29 that the fragrance precursor of the present invention releases a scent-emitting compound having a hydroxy group by the action of *Malassezia furfur* NBRC0656.

(Example 69, Comparative Example 13)

Deodorization Test on Odor Emitted from a Microorganism (Test Method)

A gauze impregnated with Triolein 1 g, Tricaproin 1 g and Androsterone 0.5 g was set as a substrate in a petri dish of 33 mm in diameter φ. Furthermore, 1 mL of *Staphylococcus aureus* test bacterial solution (1×10$^9$ cfu/mL) previously prepared in 0.9% physiological saline containing 0.2% L-leucine as a substrate was mixed with 3.5 µL of geranyl benzoate, and the resulting mixture was uniformly impregnated into the gauze that was set.

A cover was put on the petri dish and after hermetically sealing it, culture was performed at 37° C. for 20 hours. Sensory evaluation of the degree of pleasantness/unpleasantness of the odor on the gauze after culturing was performed by ten expert panelists according to the following evaluation criteria. The evaluation score was determined by averaging the evaluation values of the ten expert panelists (Example 69).

The degree of pleasantness/unpleasantness of the odor on the gauze after culturing was evaluated in the same manner as in Example 69 except that geranyl benzoate was not mixed (Comparative Example 13). The results are shown in Table 30.

It is known that each of Triolein, Tricaproin, Androsterone and L-leucine emits an offensive odor by the action of a microorganism.

(Evaluation Criteria of Degree of Pleasantness/Unpleasantness)

+4: Extremely pleasant

+3: very pleasant

+2: pleasant

+1: slightly pleasant
0: neither pleasant nor unpleasant
−1: slightly unpleasant
−2: unpleasant
−3: very unpleasant
−4: extremely unpleasant

TABLE 30

|  | Example 69 | Comparative Example 13 |
|---|---|---|
| Degree of pleasantness/unpleasantness | 1.2 | −3 |

It was confirmed from the results in Table 30 that as revealed by Comparative Example 13, an offensive odor was emitted along with proliferation of *Staphylococcus aureus* under the test conditions above. In addition, it could be confirmed that as revealed by Example 69, geranyl benzoate that is a fragrance precursor can alleviate the degree of unpleasantness of the offensive odor caused by *Staphylococcus aureus*.

Examples 70 to 72

Deodorizing mists were prepared according to the formulation shown in Table 31.

TABLE 31

| Formulation of deodorizing mist (mass %) | | | |
|---|---|---|---|
|  | Example 70 | Example 71 | Example 72 |
| Citronellyl phenylacetate | 1 | 0 | 0 |
| Compound of Example 13 | 0 | 1 | 0 |
| Compound of Example 12 | 0 | 0 | 1 |
| Polyoxyethylene(60) hydrogenated castor oil | 3 | 3 | 3 |
| Deionized water | 96 | 96 | 96 |
| Total (mass %) | 100 | 100 | 100 |

(Examples 73 to 75, Comparative Examples 14 to 16) Deodorization Test on Worn Sock Odor by Deodorizing Mist (Test Method)
A cleaned chemical-fiber sock for right foot was sprayed with 0.6 g of each of deodorizing mists obtained in Examples 70 to 72 (Examples 73 to 75). Cleaned chemical-fiber socks for left foot, which were not sprayed with the deodorizing mist, were Comparative Examples 14 to 16. Sensory evaluation of the degree of pleasantness/unpleasantness of the odor on the sock after wearing for 15 hours was performed by ten expert panelists according to the evaluation criteria. As for the evaluation criteria, the evaluation criteria of Example 69 were used. The evaluation score was determined by averaging the evaluation values of the ten expert panelists. The results are shown in Table 32.

TABLE 32

|  | Deodorizing Mist | Foot on which Sock Worn | Degree of Pleasantness/ Unpleasantness |
|---|---|---|---|
| Example 73 | Example 70 | right foot | 2.2 |
| Comparative Example 14 | none | left foot | −2.4 |

TABLE 32-continued

|  | Deodorizing Mist | Foot on which Sock Worn | Degree of Pleasantness/ Unpleasantness |
|---|---|---|---|
| Example 74 | Example 71 | right foot | 2.4 |
| Comparative Example 15 | none | left foot | −2.2 |
| Example 75 | Example 72 | right foot | 2 |
| Comparative Example 16 | none | left foot | −2 |

The socks of Comparative Examples 14 to 16 not sprayed with the deodorizing mist of the present invention emitted an offensive odor and were felt to be unpleasant, but the odor of the socks of Examples 73 to 75 sprayed with the deodorizing mist of the present invention did not smell unpleasant. It could be confirmed that a deodorizing component is released from citronellyl phenylacetate, the compound of Example 13, and the compound of Example 12, which are fragrance precursors, and the unpleasant sensation is thereby alleviated.

Example 76

A deodorizing spray was prepared according to the formulation shown in Table 33.

TABLE 33

| Formulation of deodorizing spray (mass %) | |
|---|---|
|  | Example 76 |
| Compound of Example 3 | 0.5 |
| Ethanol | 19.5 |
| LPG | 80 |
| Total (mass %) | 100 |

(Example 77, Comparative Example 17)
Deodorization Test on Sweaty Shirt by Deodorizing Spray (Test Method)
A right-side underarm portion of a cleaned cotton shirt was sprayed with 1 g of the deodorizing spray obtained in Example 76 (Example 77). In Comparative Example 17, the deodorizing spray was not sprayed onto the left-side underarm portion of the shirt. After wearing the shirts for 24 hours, sensory evaluation of the degree of pleasantness/unpleasantness of the odor in the right-side underarm portion and left-side underarm portion of the shirt was performed by ten expert panelists according to the evaluation criteria. As for the evaluation criteria, the evaluation criteria of Example 69 were used. The evaluation score was determined by averaging the evaluation values of the ten expert panelists. The results are shown in Table 34.

TABLE 34

|  | Example 77 | Comparative Example 17 |
|---|---|---|
| Degree of pleasantness/unpleasantness | 1.8 | −3.2 |

The left-side underarm portion of the shirt not sprayed with the deodorizing spray of the present invention emitted an offensive odor and was felt to be unpleasant, but the odor in the right-side underarm portion of the shirt sprayed with the deodorizing spray of the present invention did not smell unpleasant. It could be confirmed that an aromatic component is released from the compound of Example 3, which is a fragrance precursor, and the unpleasant sensation is thereby alleviated.

While the present invention has been described in detail and with reference to specific embodiments thereof, it will be apparent to one skilled in the art that various changes and modifications can be made therein without departing from the spirit and scope of the present invention. This application is based on Japanese Patent Application (Patent Application No. 2017-184026) filed on Sep. 25, 2017, the contents of which are incorporated herein by way of reference.

INDUSTRIAL APPLICABILITY

The compound represented by general formula (1) can release a fragrance alcohol, a phenol or a phenol derivative, which are an aromatic component or a deodorizing component, by the action of a hydrolase or a microorganism and therefore, is useful.

Blending of the compound represented by general formula (1) of the present invention in a fragrance composition or various products enables development of a product capable of causing a lingering scent with fresh feeling to last on the clothing, hair or skin or responding to a wide range of needs for deodorization, and therefore, the compound has applicability in the fragrance industry.

The invention claimed is:

1. A method for releasing a fragrance alcohol, a phenol or a phenol derivative, comprising reacting a fragrance precursor of the following formula (1) with a microorganism in a microbial culture,

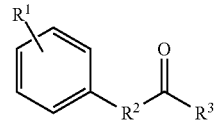

(1)

wherein $R^1$ represents a hydrogen atom, an alkyl group having a carbon number of 1 to 12, a hydroxy group, a methoxy group or an ethoxy group; $R^2$ represents a single bond, an alkylene group having a carbon number of 1 to 2, which may have a substituent, or a vinylene group which may have a substituent; and $R^3$ represents a residue resulting from removal of one hydrogen atom of a hydroxy group from a fragrance alcohol having a carbon number of 5 to 20 or a phenol which may have a substituent, wherein the microorganism is one or more species selected from the group consisting of *Bacillus subtilis* and *Moraxella osloensis*, an amount of the microorganism in the microbial culture is from $10^3$ to $10^{12}$ cfu/mL, and a mass of the fragrance precursor at the time of mixing with the microbial culture is from 0.01 to 10 mg per 1 mL of the microbial culture.

* * * * *